United States Patent [19]
McKnight et al.

[11] Patent Number: 4,935,349
[45] Date of Patent: Jun. 19, 1990

[54] EXPRESSION OF HIGHER EUCARYOTIC GENES IN ASPERGILLUS

[75] Inventors: Gary L. McKnight, Seattle; Alan Upshall, Bothell, both of Wash.

[73] Assignee: ZymoGenetics, Inc., Seattle, Wash.

[21] Appl. No.: 946,873

[22] Filed: Jan. 9, 1987

Related U.S. Application Data

[63] Continuation-in-part of Ser. No. 820,519, Jan. 17, 1986, abandoned.

[51] Int. Cl.$^5$ ............... C12P 21/00; C12N 15/00; C12N 1/14; C07H 15/12
[52] U.S. Cl. ............... 435/69.5; 435/69.6; 435/171; 435/172.3; 435/212; 435/254; 435/320; 435/91.3; 435/917; 530/351; 530/387; 536/27; 935/6; 935/10; 935/24; 935/34; 935/36; 935/48; 935/60; 935/68
[58] Field of Search ............ 435/68, 70, 91, 171, 435/252.3, 172.3, 254, 913.9 A, 320; 935/61, 24, 31, 36, 60, 61, 68, 48; 536/27

[56] References Cited

U.S. PATENT DOCUMENTS 4,486,533 12/1984 Lambowitz .............. 435/172.3
4,599,311 7/1986 Kawasaki .............. 435/71

FOREIGN PATENT DOCUMENTS 2116567 9/1983 United Kingdom ............ 435/172.3

OTHER PUBLICATIONS

Valenzuela et al, 1982 Nature 298:347-350.
McKnight et al. (1985 J. Cell Biochem & Supp. (A Part C) p. 184 Abstr. 1603.
Alber et al. 1982 J. Mol Appl. Genetics (51:419-434.
Pennica et al. 1983 Nature 301:214-221.
Ellison et al. 1982 PNAS 79:1984-1988.
Cantrell et al. 1985 PNAS 82:6250-6254.
Wong et al. 1985 Science 228:810-815.
H. M. Sealy-Lewis et al., "Regulation of Two Alcohol Dehydrogenases in Aspergillus nidulans", Curr. Gen. 8:253-259, 1984.
R. A. Lockington et al., "Cloning and Characterization of the Ethanol Utilizing Regulon in Aspergillus nidulans", Gene 33:137-149, 1985.
B. Berse et al., "Cloning and Characterization of the Ornithine Carbamoyltransferase Gene from Aspergillus nidulans", Gene 25:109-117, 1983.
C. H. Doy et al., "Genomic Clones of Aspergillus nidulans Containing alcA, the Structural Gene for Alcohol Dehydrogenase and AlcR, a Regulatory Gene for Ethanol Metabolism", DNA 4:105-114, 1985.
G. L. McKnight et al., "Identification and Molecular Analysis of a Third Aspergillus nidulans Alcohol Dehydrogenase Gene", EMBO J. 4:2093-2099, 1985.
M. M. Yelton et al., "Transformation of Aspergillus nidulans by Using a trpC Plasmid", Proc. Natl. Acad. Sci. USA 81:1470-1474, 1984.
J. Tilburn et al., "Transformation by Integration in Aspergillus nidulans" Gene 26:205-221, 1983.
M. M. Yelton et al., "A Cosmid for Selecting Genes by Complementation Aspergillus nidulans: Selection of the Developmentally Regulated yA Locus", Proc. Natl. Acad. Sci. USA 82:834-838, 1985.
J. M. Kelly and M. J. Hynes, "Transformation of Aspergillus niger by the amdS Gene of Aspergillus nidulans", EMBO J. 4:475-479, 1985.
D. J. Ballance et al., "Transformation of Asperigillus nidulans by the Orotidine-5'-Phosphate Decarboxylase Gene of Neurospora crassa", Biochem. Biophys. Res. Comm. 112:284-289, 1983.
F. P. Buxton et al., "Transformation of Aspergillus niger Using the argB Gene of Aspergillus nidulans", Gene 37:207-214, 1985.

Primary Examiner—Elizabeth C. Weimar
Assistant Examiner—Richard C. Peet
Attorney, Agent, or Firm—Seed and Berry

[57] ABSTRACT

A method for expressing higher eucaryotic genes in Aspergillus through the use of a recombinant plasmid capable of integration into the chromosomal DNA of Aspergillus is disclosed. It is preferred to utilize a transcriptional promoter within a DNA construct contained in the plasmid that is of a DNA sequence encoding an ADH enzyme or a TPI enzyme. Promoters capable of directing the expression of a heterologous gene in Aspergillus, as well as other filamentous fungal genera are also disclosed.

10 Claims, 28 Drawing Sheets

FIG. 1A

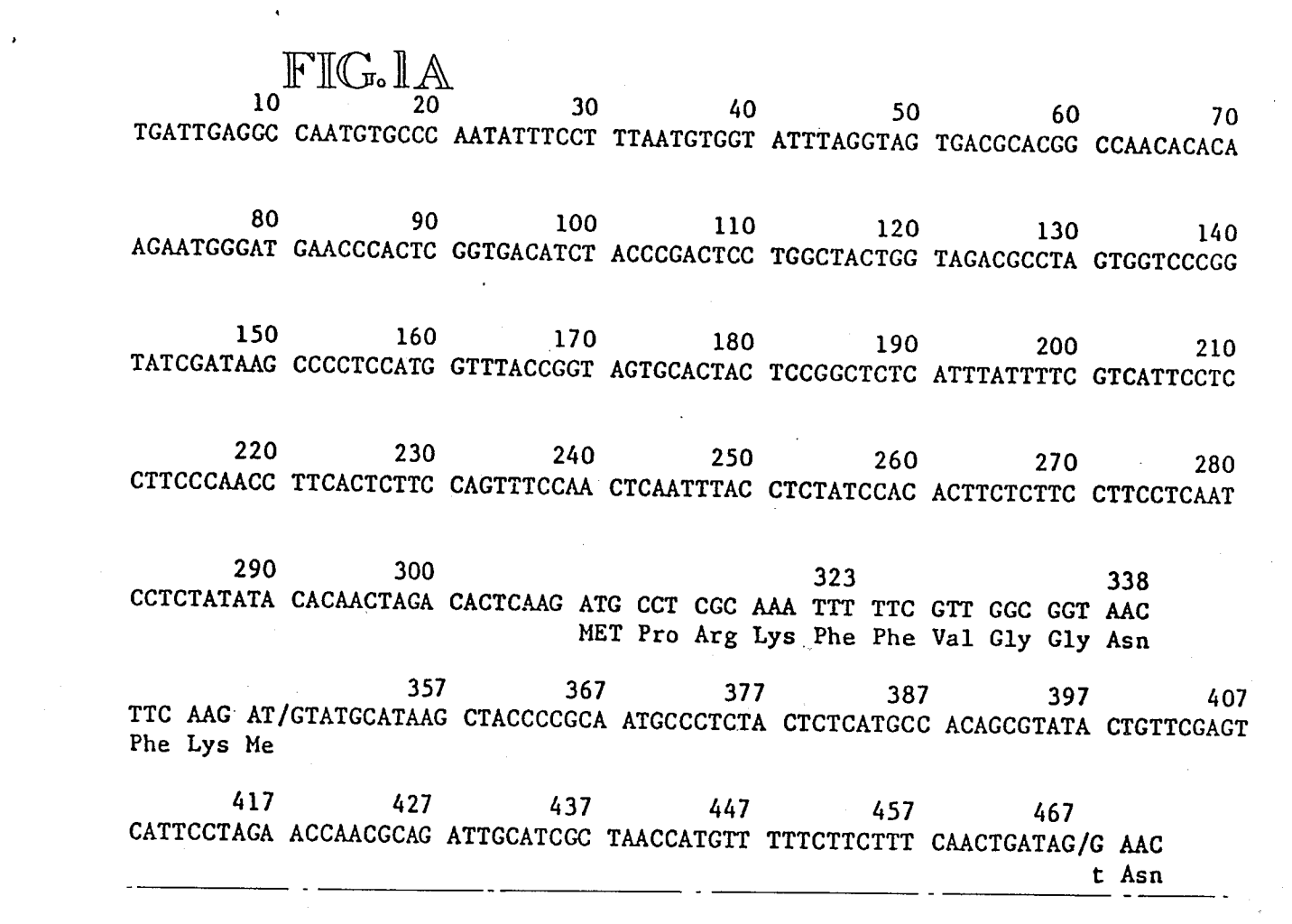

```
         10         20         30         40         50         60         70
TGATTGAGGC CAATGTGCCC AATATTTCCT TTAATGTGGT ATTTAGGTAG TGACGCACGG CCAACACACA 80         90        100        110        120        130        140
AGAATGGGAT GAACCCACTC GGTGACATCT ACCCGACTCC TGGCTACTGG TAGACGCCTA GTGGTCCCGG 150        160        170        180        190        200        210
TATCGATAAG CCCCTCCATG GTTTACCGGT AGTGCACTAC TCCGGCTCTC ATTTATTTTC GTCATTCCTC 220        230        240        250        260        270        280
CTTCCCAACC TTCACTCTTC CAGTTTCCAA CTCAATTTAC CTCTATCCAC ACTTCTCTTC CTTCCTCAAT 338
        290        300                     323
CCTCTATATA CACAAACTAGA CACTCAAG ATG CCT CGC AAA TTT TTC GTT GGC GGT AAC
                                 MET Pro Arg Lys Phe Phe Val Gly Gly Asn 357        367        377        387        397        407
TTC AAG AT/GTATGCATAAG CTACCCCGCA ATGCCCTCTA CTCTCATGCC ACAGCGTATA CTGTTCGAGT
Phe Lys Me 417        427        437        447        457        467
CATTCCTAGA ACCAAGCCAG ATTGCATCGC TAACCATGTT TTTCTTCTTT CAACTGATAG/G AAC
                                                                   t Asn
```

FIG. 1B

```
     483                498                513
GGT AAT GCC GAG AGC ACT ACC TCC ATC ATC AAG AAC CTC AAC TCT GCC AAC CTG
Gly Asn Ala Glu Ser Thr Thr Ser Ile Ile Lys Asn Leu Asn Ser Ala Asn Leu 528                543                558                573
GAT AAG TCC GTC GAA GTT GTC GTC TCT CCT CCT GCG CTC TAC CTA CTC CAG GCC
Asp Lys Ser Val Glu Val Val Val Ser Pro Pro Ala Leu Tyr Leu Leu Gln Ala 588                603                618                633
CGC GAG GTC GCC AAC AAG GAG ATT GGA GTT GCT GCC CAG AAC GTC TTC GAC AAG
Arg Glu Val Ala Asn Lys Glu Ile Gly Val Ala Ala Gln Asn Val Phe Asp Lys 648                663                678
CCC AAT GGT GCT TTC ACC GGT GAG ATC AGC GTC CAG CAG CTT CGC GAG GCC AAC
Pro Asn Gly Ala Phe Thr Gly Glu Ile Ser Val Gln Gln Leu Arg Glu Ala Asn 693                708                723                738
ATC GAC TGG ACC ATC CTT GGA CAC AGT GAG CGC CGC GTT ATC CTC AAG GAG ACT
Ile Asp Trp Thr Ile Leu Gly His Ser Glu Arg Arg Val Ile Leu Lys Glu Thr 757                777                787                797
GAT GAG/GTATGCCCCAC TGAAACACTT CGTGGTGATA CGAGCTTGAG TGCTTAAAGA TCTAG/TTC
Asp Glu                                                                Phe
```

FIG. 1C

```
                          817                                    832                                    847
              ATT GCT CGC AAG ACT AAG GCT GCC ATT GAG GGT GGC CTG CAA GTG ATT TTC TGC
              Ile Ala Arg Lys Thr Lys Ala Ala Ile Glu Gly Gly Leu Gln Val Ile Phe Cys 862              877              887              897              907              917         927
              ATC GGT GAG ACC CTT GAG/GTATGACTCT TTTTTGTT CGGCTTATCC CGATTACCCA CTTTGACTGG
              Ile Gly Glu Thr Leu Glu 937              947              957              967                        989
              GCATTCCCCT ATGTTGAGCT TTCTACCGTA TTAACAATGC GTACCAG/GAG CGT GAG GCC AAC
                                                                     Glu Arg Glu Ala Asn 1004              1019                                  1034
              AAG ACC ATC GAT GTA GTC ACT CGT CAG CTC AAC GCG GCG GCT AAG GAG CTC TCC
              Lys Thr Ile Asp Val Val Thr Arg Gln Leu Asn Ala Ala Ala Lys Glu Leu Ser 1049                        1064                        1079                        1098
              AAG GAG CAG TGG GCC AAG GTT GTC ATC GCC TAC GAG CCC CTT TG/GTAAGACACCC
              Lys Glu Gln Trp Ala Lys Val Val Ile Ala Tyr Glu Pro Val Tr 1108              1118              1128              1138              1148
              ATCTGTCTGC GCCTCGTCTC ACTGAGAGCA AACGGGCTAA TTGTGTTACAG/G GCC ATT GGA
                                                                            p Ala Ile Gly 1165                   1180                             1195                        1210
              ACC GGT AAG GTC GCT ACA ACC GAG CAG GCC CAG GAA GTC CAC TCT GCC ATC CGC
              Thr Gly Lys Val Ala Thr Thr Glu Gln Ala Gln Glu Val His Ser Ala Ile Arg
```

FIG. 1D

```
        1225                        1240                         1255
AAG TGG CTG AAG GAC GCC ATC TCC GCT GAG GCC GCT GAG AAC ACC CGG ATC ATT
Lys Trp Leu Lys Asp Ala Ile Ser Ala Glu Ala Ala Glu Asn Thr Arg Ile Ile
1270                        1285                        1300                        1315
TAT GGC GGC TCA GTG AGT GAG AAG AAC TGC AAA GAT CTC GCG AAG GAG GCC GAT
Tyr Gly Gly Ser Val Ser Glu Lys Asn Cys Lys Asp Leu Ala Lys Glu Ala Asp
                 1330                        1345                 1360             1373    1383
ATC GAT GGC TTC CTC GTC GGC GCC AGC CTT AAG CCT GCC T/GTACGTCTT TCCCTCCCCT
Ile Asp Gly Phe Leu Val Gly Ala Ser Leu Lys Pro Ala P
                                                                              1441
    1393           1403          1413           1423
TGTCGTTTCT TCGGAGTGCA TTGTTGCTTA CTAGTACTTA G/TC GTC GAT ATT GTC AAT GCC
                                              he Val Asp Ile Val Asn Ala
              1463           1473          1483          1493          1503       1513
CGC CTG TAA GCTTTGCGA GAAAAGTAAT ATTACATAAA AGGCAATAAC TATACAATAT TCATGGCGAT
Arg Leu
      1523          1533          1543          1553          1563          1573        1583
TGGATGGTCA CCTTTTGAAG ATTTGGTGTC GCAACGATTC TACCAAAAAC CATAGGCCAGC TCCGACATGT
      1593          1603          1613          1623          1633         1643        1653
AAAGAGGAAG CTTGTGTATT ATCGTCATAC TACTTAGTTA AAAATAAAAC CGTGAAAAAT TCTTATTTAC
```

FIG. 1E

```
      1663       1673       1683       1693       1703       1713       1723
TGGGCCCCTC GGGTCTAGGT AGTAATTTCT TTAAAAGCAT GACAAGGTAT ATGCATTTAG TATAATCCAC 1733       1743       1753       1763       1773       1783       1793
CCACATCCTA GAAAGCCCTT AGGAAGAATA CGACACCGAA ACACCCGACAC CGCGCCAGTA CGACGTCGGA 1803       1813       1823       1833       1843       1853       1863
GGGCCTCCAC TGCTCCCCTG CGCACCTGCC GTAGCTTAAG AATTTGCATA CCAGGAAGGT GAGAACGAAC 1873       1883       1893
TCGGTCCAAG CCCGACACCA GCGCTCACAA GGAGCTC
```

FIG. 5A

```
         10         20         30         40         50         60         70
GCATGCTTCT GCTACCTGCC TTGATTGCTG CTGCTTCTGA TAAAATCGAG TGCTATAGAC TGGGAAAGA 80         90        100        110        120        130        140
CCGAGAAGGA AGCCGTTCGT CCCGGTCATC CGGCCTCTCT CGGCTCACGAC CTTCCATCGG AACAATCAAC 150        160        170        180        190        200        210
CCCTCTTTGC CAACACGAAC CAGGCACTGC AAGCTGGGGC TGGGCCCGACT TAATGCGGTT CTAGTAGCGG 220        230        240        250        260        270        280
GGATCTGATA ATAGACGGTC TCTATAGCCA GCGTTCCCTCG TATGCCATCTG GGGTTTCGGG TTTCAGGATG 290        300        310        320        330        340        350
TCTTTCCCCC CACGCTTTTC CCGCGATTGG AAGCTGCGGA GAGAGAGTTT GGTTCCATG ACGTCTATGC 360        370        380        390        400        410        420
CGTCTGCCAT GTCCCGCCAT CCCGACAGCC ATGGATCGGG ATACTCAACC ACTTAAAACT CACTTGAGAC
```

FIG. 5B

```
430        440        450        460        470        480        490
GTTTGGTGCG AAATACTTTC CAAGAGTGGC TTGTGGCATA TACATGTTTA CTGGCCTGTC TGGGGAATTT 500        510        520        530        540        550        560
CGTCCCTAAT TGGATTGATC ATGCAGTAAG CCCGAGGATG ACCGGCCCCGG CCGAGAGACC AAAAGCCAGC 570        580        590        600        610        620        630
TCTAGGCTCG GTGACTGCTT CCTTGTCAGT GTCTCCCTGGC ACCAAACCCC TGTCCTGCCA CTGGATCCTT 640        650        660        670        680        690        700
CTTGTTCGAC GTCACTCGAT CCCAATTCAC TTCCGGCCAT GAGCGGACAT CACCCCACCT GTCCGTCATA 710        720        730        740        750        760        770
CCCGGCAACA CCACCAGGAC GCAACTACAT AAAGCCACGA AGGACTCACG CCCCTTGACC TGGAAGACCC 780        790        800        810        820        830        840
TGATTATTCG TCTCACATAG ACATCAATTG CATTCATCAG CCTCACATCA CTTGGTATCT TTGTCATTTA 850        860                                                          884                    899
CTATCTCATC CGAATCCCAG ACTGCCAAT ATG ACT ATC CCG GAG AAG CAA TGG GCC CAA
                                   MET Thr Ile Pro Glu Lys Gln Trp Ala Gln
```

FIG. 5C

```
                914                929                944
GTC GTC GAG AAG GGT GGA CCC CCT GTC TAC AAG CAG ATT CCC GTG GCA AAG
Val Val Glu Lys Gly Gly Pro Pro Val Tyr Lys Gln Ile Pro Val Ala Lys
      959                974                989                1004
CCT GGC CCG GAC GAG ATC TTG GTC AAG ATC CGG TAT ACC GGG GTT TGC CAT ACC
Pro Gly Pro Asp Glu Ile Leu Val Lys Ile Arg Tyr Thr Gly Val Cys His Thr
            1019               1034               1049
GAC TTG CAC GCC ATG AAG GGT GAC TGG CCA CTC GGG TTG AAG CTT CCC CTC GTG
Asp Leu His Ala MET Lys Gly Asp Trp Pro Leu Gly Leu Lys Leu Pro Leu Val
1064               1079               1094               1109
GGC GGA CAT GAA GGA GCT GGC GTG GTC GCC ACG GGT GAC CTC GTC AAT GAG
Gly Gly His Glu Gly Ala Gly Val Val Ala Thr Gly Asp Leu Val Asn Glu
                1124               1139               1154               1169
TTC GAA GTT GGA GAT CAC GCT GGT ATC AAA TGG TTG AAC GGA TCC TGT TTG GCT
Phe Glu Val Gly Asp His Ala Gly Ile Lys Trp Leu Asn Gly Ser Cys Leu Ala
            1184               1199               1214
TGT GAG TTC TGC AAG CAG GCC GAG GAG CCC CTG TGT CCT CAC CCG TTG CTA TCC
Cys Glu Phe Cys Lys Gln Ala Glu Glu Pro Leu Cys Pro His Ala Leu Leu Ser
```

FIG. 5D

```
1229                    1244                         1259                          1274
GGT TAC ACC GTC GAT GGT ACG TTC CAG CAG TAT GCC ATC GCC AAG GCC AGT CAT
Gly Tyr Thr Val Asp Gly Thr Phe Gln Gln Tyr Ala Ile Ala Lys Ala Ser His 1289                         1304                         1319
GCG TCG AAG CTC CCG AAG GAA GTT CCC CTT GAT GCT GTC GCT CCC ATC CTC TGT
Ala Ser Lys Leu Pro Lys Glu Val Pro Leu Asp Ala Val Ala Pro Ile Leu Cys 1334                    1349                         1364                         1379
GCT GGT ATC ACT GTC TAC AAG GGA TTG AAG GAG TCT GGT GCT CGT CCC GGC CAG
Ala Gly Ile Thr Val Tyr Lys Gly Leu Lys Glu Ser Gly Ala Arg Pro Gly Gln 1394                         1409                         1424                1439
ACC GTC GCC ATT GTC GGC GCC GGA GGT GGA CTC GGA TCG CTG GCT CTG CAG TAT
Thr Val Ala Ile Val Gly Ala Gly Gly Gly Leu Gly Ser Leu Ala Leu Gln Tyr 1454                         1469                         1484
GCT AAG GCA ATG CTT GGG CTT CGC ACC ATC GCC ATC GAC GGT GGT GAC GAG AAG AAA
Ala Lys Ala MET Leu Gly Leu Arg Thr Ile Ala Ile Asp Gly Gly Asp Glu Lys Lys 1499                    1514                         1530           1540           1550      1560
GCT ATG TGC GAG AAA CTC GGA TCG GAG/GTAAATGTCT CAGTCCCCAA TACCACCACA TCTGGCTAAC
Ala MET Cys Glu Lys Leu Gly Ser Glu

1570
CCTCTCTCTC TATCCAG/GCA TAC ATC GAC TTT AAG ACA TCC AAG GAT GTA GTT GAG
                    Ala Tyr Ile Asp Phe Lys Thr Ser Lys Asp Val Val Glu
                         1592                        1607
```

FIG. 5E

```
     1622                 1637                     1652                        1667
GAC GTC AAG GCA GCC ACT CCG GAA GGC CTT GGT GCC CAC GCT GTG ATT CTT CTC
Asp Val Lys Ala Ala Thr Pro Glu Gly Leu Gly Ala His Ala Val Ile Leu Leu 1682                     1697                    1712
GCT GTG GCC GAA AAG CCC TTC CAG CAG GCA ACC GAG TAC GTT CGC TCC AAG GGT
Ala Val Ala Glu Lys Pro Phe Gln Gln Ala Thr Glu Tyr Val Arg Ser Lys Gly 1727                    1742                     1757                    1772
AGT GTC GTC GCT ATT GGC ATG CCA GCC GGC GCA TTC CTT CGA GCC CCT GTC TTC
Ser Val Val Ala Ile Gly MET Pro Ala Gly Ala Phe Leu Arg Ala Pro Val Phe 1787                     1802                    1817                 1832
AAC ACC GTT GTC CGT ATG ATC AAC ATC AAG GGA AGC TAC GTT GGC AAT AGG CAG
Asn Thr Val Val Arg MET Ile Asn Ile Lys Gly Ser Tyr Val Gly Asn Arg Gln 1847                     1862                    1877
GAT GGC GTA GAA GCA GTA GAC TTC TTT GCC CGC GGA CTC ATC AAG GCT CCG TTC
Asp Gly Val Glu Ala Val Asp Phe Phe Ala Arg Gly Leu Ile Lys Ala Pro Phe 1892                    1907                    1922                        1941
AAG ACG GCT CCT TTG GAG GAT TTG CCG CGC ATC TTC GAA CTG ATG G/GTACGTTGT
Lys Thr Ala Pro Leu Glu Asp Leu Pro Arg Ile Phe Glu Leu MET G
```

```
      1951       1961       1971       1981                 2000
ATACCTAGTG ATATTAAGTC GAGTTACTAA CTATGAAAAC AG/AA CAA GGC CAG ATC GCC GGT
                                            lu Gln Gly Gln Ile Ala Gly 2015             2030       2040       2050       2060       2070
CGG TAT GTC CTT GAG GTG CCT CAG GTG TAA GCAGGTAGAC ACGGAAAGAT TTGGCCTTGG GGATGACACG
Arg Tyr Val Leu Glu Val Pro Gln 2080       2090       2100       2110       2120       2130       2140
AGTTGCTGGT CAGACGGAGT TTATTTACCA GTCTCGAGCA TGACTACTAT GATGGGCTTA TGACTACTAA 2150       2160       2170       2180       2190       2200       2210
TAACGTCTCT CTGACATGTT TAAAATACTG AAATAATTGA ATCTTCTATA CTCTTATTCA CCATATCCGC 2220       2230       2240       2250       2260       2270       2280
ACGTGATGGA TACCAAGTAA TTGACTCTAC ATGGAGAGCA CGCACGGCAA GCCTTGCTGC AAATTAGATT 2290       2300       2310       2320       2330       2340       2350
GTCTCATGTC ATCCATCATG CATAAGCATC ATCACATCGC CATGGCCCTGC ATGACTACCT AATATCTGTT

2360
CAGATACCTA GTGGTACAA
```

```
         10         20         30         40         50         60         70
ATACCTAAAT TCTTTCTCA CTTTCTTCCA CAATTCCCTT CTTCAGACAC TCTCCCCGTC TTTTCCAATC 80                    104                   119                   135
ACACCAACAC ATCTTCAAA ATG CCT CGT CAA TTC TTC GTG GGT GGT AAC TTC AAG AT/GTATGGGA
                     MET Pro Arg Gln Phe Phe Val Gly Gly Asn Phe Lys Me 145         155         165         175         185         195         205
ACCCCTCCAT CCGGTGCCCC GCCAGCTCTT CCACCAAAAA CTGCTTCACC CTCAACGAGC CCGGTGGCTA 215         225         235                   251
ACGGACTGATT TCTACGTTGC TCTCACACAG/G AAG GGT ACT GCG GAC AGC ATT ACC TCC
                                   t Asn Gly Thr Ala Asp Ser Ile Thr Ser 266                                     281                                  296                                 311
ATC ATC AAG AAC CTC AAT GCC GCC AAG TTG GAC GAG TCC GCC GAG GTG GTT GTC
Ile Ile Lys Asn Leu Asn Ala Ala Lys Leu Asp Glu Ser Ala Glu Val Val Val 326                                 341                                 356                                 371
TCT CCC ACC CTC TAC CTG CTC CCC GCC CGC CAG GCC GCC CAG GCC GAG AAG ATC
Ser Pro Thr Leu Tyr Leu Leu Pro Ala Arg Gln Ala Ala Gln Ala Gly Glu Lys Ile 386                                 401                                 416
GGC GTC GCC GCC CAG AAC GTC TTC GAC AAC CCC AAT GGT GCT TTC ACC GGT GAG
Gly Val Ala Ala Gln Asn Val Phe Asp Asn Val Phe Pro Lys Asp Asn Gly Ala Phe Thr Gly Glu
```

FIG. 8B

```
    431                  446                  461                  476
ATC AGT GTT GAG CAG CTC CGT GAT GTC AAG ATC GAC TGG ACC ATC ATC GGT CAC
Ile Ser Val Glu Gln Leu Arg Asp Val Lys Ile Asp Trp Thr Ile Ile Gly His 491                  506                  525             535
AGC GAG CGC CGT GTC ATC CTG AAG GAG AGC GAC GAG/GTAGGTCTAC CCCGCCAAAT
Ser Glu Arg Arg Val Ile Leu Lys Glu Ser Asp Glu 545              555              565                          589
ATTATGGTTT GGGTTGGGCT AATTTAATGC CCCATCTAG/TTC ATT GCC CGC AAG GTC AAG
                                           Phe Ile Ala Arg Lys Val Lys 604                  619                  634             649
GCC GCC ATT GAC GGT GGC CTC AGC GTT ATC TTC TGC ATT GGT GAG ACT CTT GAG/
Ala Ala Ile Asp Gly Gly Leu Ser Val Ile Phe Cys Ile Gly Glu Thr Leu Glu 659        669        679        689        699        709     719
GTATGTCGGC CTGTAGTTTT TTGCTTTTTG TCTCTTTTGAC TTCTGCGACT ACCCCTCTTC GAGCTCGCGG 729        739        749        759                774
TGACCCGGTG AGATGAACCG AGACTAATGC AACCCCCCAG /GAG CGT GAG GCC AAC AAG ACC
                                             Glu Arg Glu Ala Asn Lys Thr
```

FIG. 8C

```
     789                804                819                834
ATC GAC GTT GTC ACC AAG CAG CTC AAC GCT GTT GCC AAG GAG CTC ACC AAG GAG
Ile Asp Val Val Thr Lys Gln Leu Asn Ala Val Ala Lys Glu Leu Thr Lys Glu
                     849                864                880        890
CAG TGG GCT AAG GTT ATC GCC TAC GAG CCC GTC TG/GTAAGTTC ACGATCATTT
Gln Trp Ala Lys Val Val Ile Ala Tyr Glu Pro Val Tr
     900           910           920           930           947
CGTCTGGCCT TGCTCGTCGC ACGTGCGCTA ACCCATTCA G/G GCT ATC GGT ACC GGC AAG
                                           P Ala Ile Gly Thr Gly Lys
                    962               977                992
GTC GCC ACG GCC CAG GCC CAG GAG GTC CAC GCT GCT ATC CGC AAG TGG CTC
Val Ala Thr Ala Gln Ala Gln Glu Val His Ala Ala Ile Arg Lys Trp Leu
1007              1022               1037              1052
GTC GAT GCC ATC TCT GCC GAG GCT GCC GAC AAC ACC CGC ATC ATC TAC GGT GGT
Val Asp Ala Ile Ser Ala Glu Ala Ala Asp Asn Thr Arg Ile Ile Tyr Gly Gly
             1067              1082              1097              1112
TCC GTC AGC GAG AAG AAC TGC CGT GAC GCC AAG GAG GCC GAT GTC GAC GGT
Ser Val Ser Glu Lys Asn Cys Arg Asp Ala Lys Glu Ala Asp Val Asp Gly
       1127              1142              1155         1165       1175
TTC CTG GTT GGC GGT GCC AGC TTG AAG CCT GCT T/GTATGTGTA ACCTTTCATT TGGCTAATGC
Phe Leu Val Gly Gly Ala Ser Leu Lys Pro Ala P
```

FIG. 8D

```
     1185       1195       1205                 1220
GAGATGTACT AATTTCTTTT AACTCCAG/TC GTT GAC ATC ATC AAC GCT CGT CTG TAA
                              he Val Asp Ile Ile Asn Ala Arg Leu 1242       1252       1262       1272       1282       1292       1302
ACAATTGAAC GATTGATGGA CATGTGATAT GATATCCGGA TCCCAATAGG CGGGAAGTA AGCCTGGGGA 1312       1322       1332       1342       1352       1362       1372
CTCTGCAGAC TCCATGACCA ACTGCAGAGT ATCAAAATTT ATAAAGGACA TAAAAAAACG AATTTATACC 1382       1392       1402       1412       1422       1432       1442
TATAAATCCA AATTGAATAC CACCATTAAC CTTAATTCTC CCAAACCCCT TTCTGTTACG ATAACTCGAC 1452       1462       1472       1482       1492       1502
CATTCTATCA ATTAGTACCT AGTAAGTTGC AGTATAATCA TAGCACATAT CATAGTATCT ACA
```

FIG. 12

```
CTGCAGCTTCCACGAACCTCGAGCCAAGGACTTAGAATCGGAGGAGAAACTGTCTACATAACTCTGAAG
CAGATCGGATGTCATCCGGGTGCCGGTGAGAGGTTTTGTCAGTTGCCTTGGATTCTGGCTGTG
AGTATTATTGTCGCGCAAAGAATAAGTAATTTAGTTGTGCCTCAGTTCAGAATGAGCTCTTACG
ATTACTCTTATCTACTCAGAGTATAATAGCGAGGTACTGGTGTGCCGATAGTCGCGACGGTCTAAAGTG
GGCTAAGCAAGTACCAAAACGCAATGGCACCATGTCAGCGGCTCCGATTACTTCAGAGCTGATCA
ACCCATCTCTAGGAATCTCCTGGCATTGCTTTACCGTCCGAGTCCTTCCTCCTTGGAGGTGAACTCTGAT
CTCTGTTGTAGTATGTACTTAATAGAGTGTTGTAGCAGATCCCAAGTGGGGGTTGCTGTCAGACATGGTC
CCACCCAGCGGAGCTTCCCCCGCAGTCCTTGATACTCCGCAACGAGTCTTGCCTAAAGCACTTTCAGCA
GTATTTGGTGCTACAGCCCCTGTACATCGCCACTCCAGATGAGCCATGTCACGCCACCAGTCAGAGGACCCTGGGAGACCATG
CTATAAAGGAGAGATATCGCCACTCAGACTGATAACTAGATTTGGTGCGAGGCACAGAAATGGCCTGA
TCCAGACTGGTAGGCTTACTCTGCGTGTGCCAGCAATGCTCCAAACCAGCCGGTTCTACGATGCCGAA
TCTACTCTAATATCACTCAGATCAGTCGGTCTGCCCCGGGTGTCGAGCTCCAAGGATGACATCGTCGA
CCCAATGTCTGGCCCCAATGGCCATGGAAGCCGAAATTGGCCACCAATGCCTGCCGCTACGCTCTCGGCG
CGTGCTTTAGCTGCCCGGCAAAAGCAGGAATTCGGACGATGTCCTCTCGCCTTGTGTGGATTCGTTTC
GTTGGTGGACCCCATCCCCTGTATAGTGTTGCCTTGTGTTGCACTGTTATAGCCAGTGTCTAGAGGCAGTG
CTGCTACACCCCTCATTCTCTTGTGGTATAAATGGCAAGAGACTCTCACGAAGCTTGTGAATTAGCTTG
TCTCTGTACATCCTCTCAGTTAATAGTTTATTACCTTCTCATCAATCTCATTTACACACTCTCATCCC
AAGGATCCGAATTC
```

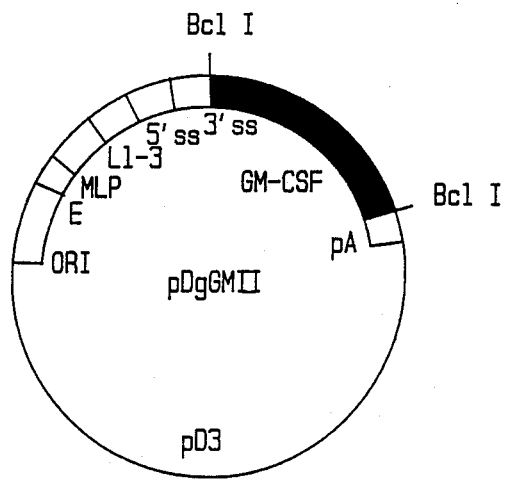
FIG.19
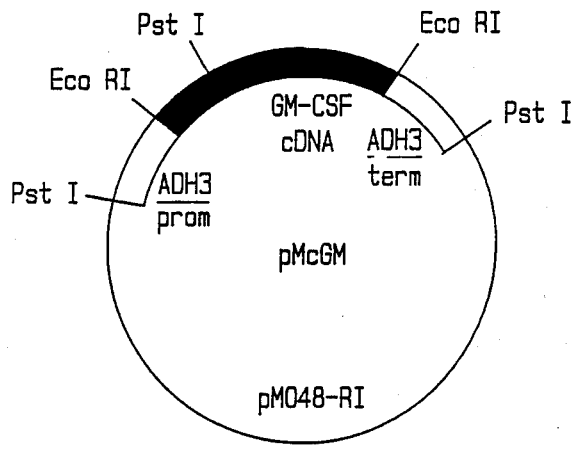

EXPRESSION OF HIGHER EUCARYOTIC GENES IN ASPERGILLUS

CROSS-REFERENCE TO RELATED APPLICATION

This application is a continuation-in-part of U.S. patent application Ser. No. 820,519, filed Jan. 17, 1986, which application is abandoned.

TECHNICAL FIELD

The present invention relates generally to the expression of foreign genes in filamentous fungi, and more specifically, to the expression of higher eucaryotic genes in Aspergillus as well as particularly advantageous promoters capable of directing the expression of heterologous genes therein.

BACKGROUND ART

The cloning and expression of foreign genes in bacteria and yeast has been demonstrated to be a viable means for the production of a variety of useful proteins. Expression of foreign genes in these microorganisms has relied on the use of autonomously replicating extrachromosomal elements, generally known as plasmids. However, these expression systems have presented numerous problems for industrial scale-up, including problems in protein solubility, purification, and secretion.

Filamentous fungal genera, such as Aspergillus and Penicillium, have a long history of industrial use in the manufacture of enzymes and specialty chemicals. The development of these organisms as industrially important producers has heretofore relied on classical methods of mutation followed by screening to obtain suitable high producing strains.

In light of this fermentation technology, it would be beneficial to develop an efficient system for expressing foreign genes in filamentous fungi. The industrial use of filamentous fungi could then be expanded to include pharmaceuticals, enzymes, and other products that are not made, or are made only inefficiently by these fungi.

Filamentous fungi present several other potential advantages over bacteria and yeast. For instance, species of filamentous fungi are known which secrete a wide variety of substances, a feature which facilitates the purification of those products. Furthermore, these organisms do not exhibit the extreme codon usage bias of yeast, which may make them more suitable for the production of some foreign proteins. Additionally, research has suggested that some species are also capable of processing intervening sequences present within the genes of higher eucaryotes, in a manner similar to higher eucaryotes, which bacteria and yeast cannot do. Filamentous fungi are also known to effect post-translational modifications of proteins, such as glycosylation and phosphorylation, in a manner similar to higher eucaryotes, which may be important to the efficacy of the proteins.

Transformation systems for filamentous fungi have been described by a number of authors. In the case of the genus Aspergillus, these systems rely on chromosomal integration of the cloned DNA. Although autonomously replicating extrachromosomal elements have been utilized to obtain expression of a heterologous gene in Neurospora (Lambowitz, U.S. Pat. No. 4,486,533), Aspergillus species generally lack extrachromosomal plasmid elements and it is believed that such elements would not function adequately in these fungi.

Reports of transformation in filamentous fungi have generally been directed to complementing mutations with wild-type DNA from the same species. Yelton et al. (Proc. Natl. Acad. Sci. USA 81: 1470–1474, 1984) transformed a trpC− strain of Aspergillus nidulans to trpC+ using a plasmid containing the complete A. nidulans trpC gene, and similarly, an argB− strain was transformed to argB+. Tilburn et al. (Gene 26: 205–221, 1983) transformed A. nidulans using the cloned amdS gene. Yelton et al. (Proc. Natl. Acad. Sci. USA 82: 834–838, 1985) used an A. nidulans cosmid library to complement several mutations in an A. nidulans strain.

Several authors have also described transformation of filamentous fungal species with DNA from closely related fungal species. Ballance et al. (Biochem. Biophys. Res. Comm. 112: 284–289, 1983) transformed an A. nidulans pyrimidine auxotroph to prototrophy using the orotidine-5′-phosphate decarboxylase gene of Neurospora crassa. Kelly and Hynes (EMBO J. 4: 475–479, 1985) transformed wild type strains of A. niger with the A. nidulans amdS gene and recovered transformants able to use acetamide as a nitrogen source. Buxton et al., (Gene 37: 207, 1985) transformed A. niger argB− mutants with the A. nidulans argB+ clone.

There is a need in the art, however, for an efficient method of producing higher eucaryotic proteins in a system that can utilize established industrial fermentation technology. The present invention fulfills this need and further provides other related advantages.

DISCLOSURE OF THE INVENTION

Briefly stated, the present invention discloses a method for expressing higher eucaryotic genes in Aspergillus, and further discloses particularly advantageous promoters capable of directing the expression of a heterologous gene in Aspergillus and in other filamentous fungal genera.

More specifically, the method noted above comprises introducing into an Aspergillus host a recombinant plasmid capable of integration into the chromosomal DNA of Aspergillus, the plasmid containing a DNA construct capable of directing the expression of foreign genes in Aspergillus. The DNA construct contains a transcriptional promoter followed downstream by a higher eucaryotic gene under transcriptional control of the promoter, the gene being followed downstream by a terminator. Subsequently, the Aspergillus host is grown in an appropriate medium, and the protein product of the higher eucaryotic gene is isolated from the culture medium in which the Aspergillus host is grown. A DNA construct and a recombinant plasmid as described above are also disclosed.

In addition, an Aspergillus culture transformed with a DNA construct capable of directing the expression of foreign genes in Aspergillus, and containing a transcriptional promoter followed downstream by a higher eucaryotic gene under transcriptional control of the promoter, the gene being following downstream by a terminator, is also disclosed.

In preferred embodiments, the promoter noted in the DNA construct, plasmid, transformed culture and method described above is that of a DNA sequence encoding an alcohol dehydrogenase (ADH) enzyme or a triose phosphate isomerase (TPI) enzyme. The DNA sequence may be a filamentous fungal gene, such as an A. nidulans gene or an A. niger gene. Particularly preferred *A. nidulans* genes are ADN3 or tpiA, while particularly preferred *A. niger* genes are adhA or tpiA.

As noted above, another major aspect of the present invention discloses a promoter capable of directing the expression of a heterologous gene in Aspergillus, wherein the promoter is that of a gene encoding a protein selected from either ADH or TPI enzymes. A method for expressing heterologous genes in Aspergillus utilizing this promoter is also disclosed.

Other aspects of the present invention will become evident upon reference to the following detailed description and attached drawings.

BRIEF DESCRIPTION OF THE DRAWINGS

FIG. 1 A through E illustrate the nucleotide sequence and translated amino acid sequence of a portion of the *A. nidulans* tpiA genomic clone. Slash marks (/) in the nucleotide sequence indicate exon-intron boundaries.

FIG. 5 illustrates the nucleotide sequence and translated amino acid sequence of the *A. niger* adh A gene. Slash marks (/) indicate exon-intron boundaries.

FIG. 8 illustrates the nucleotide sequence and translated amino acid sequence of the *A. niger* tpi A gene. Slash marks indicate exon-intron boundaries.

FIG. 12 illustrates the nucleotide sequence of the *A. nidulans* ADH3 promoter fragment from the PstI site to the BamHI and EcoRI sites.

FIG. 19 shows partial restriction maps of the plasmids pDgGMII and pMcGM. Symbols used are ori, the adenovirus 5 0-1 map unit sequence; E, the SV40 replication origin and enhancer; MLP, the adenovirus 2 major late promoter; L1-3, the adenovirus 2 tripartite leader; 5'ss and 3'ss, 5' and 3' splice sites; and pA, the SV40 early polyadenylation signal.

BEST MODE FOR CARRYING OUT THE INVENTION

Figure 2:
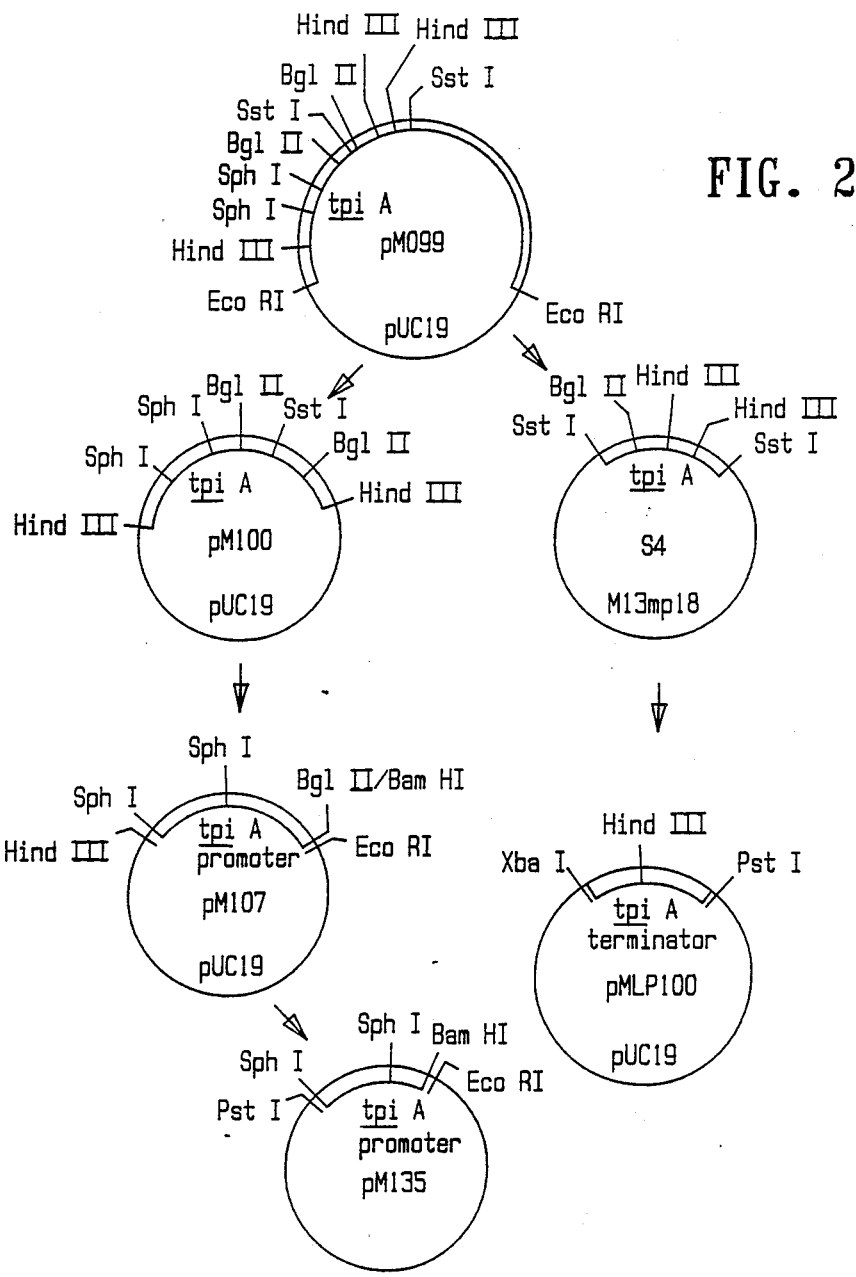
FIG. 2 illustrates the subcloning of the *A. nidulans* tpiA promoter and terminator.

Prior to setting forth the invention, it may be helpful to an understanding thereof to set forth definitions of certain terms to be used hereinafter.

Higher Eucaryotic Gene: A gene or cDNA isolated or derived from an organism other than a prokaryote or a fungus.

Within the present invention, higher eucaryotic genes may be expressed in an Aspergillus host through the use of recombinant DNA techniques. The genus Aspergillus is taxonomically within the class Ascomycetes. This classification is based upon the form of the sexual fruiting bodies, e.g. as directly applied to the species *Aspergillus nidulans*. However, it should be noted that other species are included within this genus that have no known sexual reproductive cycle; for example, *Aspergillus niger* and *Aspergillus terreus*. These species are included on the basis of their vegetative morphology, and separated on the basis of the developmental detail and shape of mature asexual reproductive structures called conidiophores (Thom and Raper, 1945 *Manual of the Aspergilli;* Balliére Tindall & Cox, London). Preferred species of Aspergillus include *A. nidulans* and *A. niger*, although it will be evident to one skilled in the art that other species of Aspergillus (available through the ATCC or the Fungal Genetics Stock Center, Arcata, CA), such as *A. terreus*, could be utilized within the present invention. Further, other fungal genera, such as Penicullium, which are separated from Aspergilli by differences in condiophore structure, could also be used since genera within the class are not generally separated on the basis of biochemical differences.

As noted above, higher eucaryotic genes include cDNA clones derived from higher eucaryotic genes. By way of example, the present invention describes the expression of proteins encoded by a tissue plasminogen activator (t-PA) gene, an immunoglubulin G (IgG) gene, and by a granulocyte macrophage colony stimulaing factor (GM-CSF) gene, although it will be evident to one skilled in the art that a variety of other higher eucaryotic genes may be expressed within the methods of the present invention. For instance, genes encoding platelet-derived growth factor (PDGF), insulin, superoxide dismutase, and erythropoietin as well as derivatives of these and other proteins may be used within the present invention.

The higher eucaryotic gene described above is contained within a DNA construct and under transcriptional control of a promoter. As used herein, a promoter may also include regulatory sequences located in the flanking 5' non-coding region of a gene. In preferred embodiments of the present invention, the promoter is that of a DNA sequence encoding an ADH enzyme or a TPI enzyme. ADH enzymes and TPI enzymes are those which catalyze particular biochemical reactions. ADH catalyzes the interconversion of ethanol and acetaldhyde, while TPI catalyzes the interconversion of glyceraldehyde-3-phosphate and dihydroxy-acetone phosphate. In preferred embodiments, the DNA sequence is a filamentous fungal gene, such as an *A. nidulans* gene or an *A. niger* gene.

Within *A. nidulans*, there are three types of known ADH genes, all regulated in a slightly different manner. Referring now to Table 1 (below), the regulated expression of the three ADH genes in the presence of a sole carbon source of either glucose or ethanol (EtOH), or glucose and ethanol together is shown.

TABLE 1

| Gene | Glucose | ETOH | Glucose + ETOH |
|---|---|---|---|
| alcA | − | + | − |
| ADH2 | + | − | − |
| ADH3 | ± | + | + |

*(−) = Off; (+) = On; and (±) = Intermediate.

In the present invention, a particularly preferred *A. nidulans* gene is ADH3, which is strongly expressed in the presence of ethanol or in glucose and ethanol. Another particularly preferred *A. nidulans* gene is tpiA, which is strongly expressed in the presence of either glucose or ethanol.

Within *A. niger*, an ADH gene has been isolated, referred to herein as adhA. At the nucleotide level of the cDNA, adhA has similarities to both alcA and ADH3. The regulatory pattern of adhA is as shown in Table 2.

TABLE 2

| | Glucose | ETOH | Glucose + ETOH |
|---|---|---|---|
| adh A | + | + | + |

*(−) = Off; (+) = On.

In addition to adhA, another particularly preferred *A. niger* gene is tpiA, which is strongly expressed in the presence of either glucose or ethanol.

Although particularly preferred ADH and TPI promoters have been identified herein, it will be evident to one skilled in the art that other ADH and TPI genes from other filamentous fungi could be utilized within the present invention. These genes may exhibit a different regulatory pattern than shown above.

Promoters and terminators for use within the present invention may be identified as the adjacent 5′ and 3′ non-translated and flanking regions, respectively. In general, sequences of approximately 1 kb in length will be sufficient to provide promoter and terminator functions.

Promoters and terminators suitable for use within the present invention may be isolated from Aspergillus genes. These genes may be identified by hybridization to cDNA probes which are isolated on the basis of their ability to complement corresponding genetic defects in the yeast *Saccharomyces cerevisiae*, although other methods of gene isolation may be used. In general, any cDNA from Aspergillus which could complement a gene defect in *Saccharomyces cerevisiae* could be isolated using the complementation procedure described herein. Suitable strains of *S. cerevisiae* may be obtained from the ATCC or the Yeast Genetics Stock Center, Berkeley, CA, or may be prepared by conventional mutagenesis techniques. Once the appropriate cDNA clone is identified, it may be used to isolate a genomic clone containing the gene of interest, and the 5′ flanking region of the gene characterized for the promoter element.

Downstream of the higher eucaryotic gene in the DNA construct of the present invention is a terminator including a polyadenylation signal. Preferred terminators include those of a DNA sequence encoding an ADH enzyme or a TPI enzyme. ADH enzymes and TPI enzymes are those enzymes having a catalytic activity as described above. In preferred embodiments, the DNA sequence is a filamentous fungal gene, such as an *A. nidulans* gene or an *A. niger* gene. In general, suitable terminators may be obtained from genes isolated as described above for the promoters.

The DNA construct containing a transcriptional promoter followed downstream by a higher eucaryotic gene, the gene being followed by a terminator as described above is contained within a recombinant plasmid capable of integration into the chromosomal DNA of Aspergillus.

In order to efficiently recover transformants, a selectable marker is included as a component of the transforming DNA. The selectable marker may be an integral part of the plasmid containing the higher eucaryotic gene to be expressed or may be part of a separate DNA construct, and incorporated into the host by co-transformation.

A requirement for the efficient production of higher eucaryotic proteins is a stable transformant, i.e., one in which the transforming DNA is maintained within the genome and is not lost during growth or propagation. Aspergillus species, in common with some other filamentous fungal species, neither harbor nor maintain extrachromosomal plasmids. To achieve stability of a transformant therefore, the transforming DNA must be integrated into the host chromosome. In order to efficiently achieve such integration, a segment of the host species DNA is included as a component of the transforming DNA. This segment provides homology to allow recombination events to occur between the chromosome and transforming DNA, these being necessary for the integration process. Even in the absence of such a homologous segment of DNA, integration of transforming DNA into the chromosome may occur, but at substantially lower frequencies.

Within the present invention, homology between the transforming DNA and the host chromosome may be provided by the selectable marker, e.g., argB, or amdS; the promoter and terminator fragments in the expression unit; or by a cDNA derived from a filamentous fungal gene.

To summarize the examples which follow, Example 1 describes the construction of an *Aspergillus nidulans* cDNA library, and the isolation of the *A. nidulans* tpiA promoter and terminator. Example 2 describes the construction of *A. niger* cDNA and genomic libraries and the isolation of DNA sequences corresponding to the tpiA and adhA genes. The adhA promoter was isolated from one of the clones. Example 3 describes the construction of expression vectors comprising a human t-PA cDNA. Included in the vectors is a secretory signal sequence, either the t-PA pre-pro sequence or the *A. niger* glucoamylase pre-pro sequence. Example 4 describes the construction of an expression vector comprising a cDNA encoding a human immunoglobulin heavy chain. Example 5 describes the cloning of a human cDNA encoding granulocyte-macrophage colony stimulating factor. This cDNA was then used in the construction of an Aspergillus expression vector. Example 6 describes the expression of t-PA, GM-CSF, and IgG in Aspergillus.

The following examples are offered by way of illustration and not by way of limitation.

EXAMPLES

Aspergillus culture media were formulated as follows:

| MINIMAL MEDIUM | | |
|---|---|---|
| Per liter: | Dextrose | 5.0 g |
| | Salt solution (below) | 50.0 ml |
| | Trace elements (below) | 1.0 ml |
| | ± Agar (Difco) | 12.5 g |
| Adjust to pH 6.5, autoclave 15 minutes. | | |

| COMPLETE MEDIUM | | |
|---|---|---|
| Per liter: | Dextrose | 5.0 g |
| | Peptone | 2.0 g |
| | Yeast extract | 1.0 g |
| | Casein hydrolysate | 1.0 g |
| | Salt solution (below) | 50.0 ml |
| | Trace elements (below) | 1.0 ml |
| | Vitamin solution (below) | 1.0 ml |
| | Nucleic acids solution (below) | 3.0 ml |
| | CM supplement (below) | 10.0 ml |
| | ± Agar (Difco) | 15.0 grams |

| SALT SOLUTION | | |
|---|---|---|
| Per liter: | $NaNO_3$ | 120.0 g |
| | KCl | 10.4 g |
| | $MgSO_4$ | 10.4 g |
| | $KH_2PO_4$ | 30.4 g |

| SORBITOL MEDIUM |
|---|
| Minimal medium with the addition of 1.2M sorbitol. |

| TRACE ELEMENT SOLUTION | | |
|---|---|---|
| Per liter: | $(NH_4)_6Mo_7O_{24}.4H_2O$ | 1.1 g |
| | $H_3BO_3$ | 11.0 g |
| | $CoCl_2.6H_2O$ | 1.6 g |
| | $CuSO_4$ | 1.6 g |
| | $Na_2EDTA$ | 50.0 g |
| | $FeSO_4.7H_2O$ | 5.0 g |
| | $MnCl_2.4H_2O$ | 5.0 g |
| | $ZnSO_4.7H_2O$ | 22.0 g |
| Dissolve components sequentially, boil, cool, adjust pH to 6.5 with KOH. | | |

| VITAMIN SOLUTION | | |
|---|---|---|
| Per liter: | Pyridoxine HCl | 1.0 g |
| | Thiamine HCl | 1.5 g |
| | p-aminobenzoic acid | 0.8 g |
| | Nicotinic acid | 2.5 g |
| | Riboflavin | 2.5 g |
| | Choline HCl | 20.0 g |
| | Biotin (500 ug/l) | 50.0 ml |

| NUCLEIC ACIDS SOLUTION | | |
|---|---|---|
| | Yeast nucleic acids, sodium salt | 100 g |
| | 2N HCl | 1.0 liter |
| Heat to 100° C., 20 min., adjust pH to 6.2 | | |

| CM SUPPLEMENTS | | |
|---|---|---|
| Per liter: | Adenine | 7.5 g |
| | L-methionine | 5.0 g |
| | L-lysine HCl | 36.5 g |
| | Riboflavin | 0.5 g |

EXAMPLE 1

Isolation of *A. nidulans* tpiA Promoter and Terminator

A. Cloning of *A. nidulans* tpiA cDNA

Five ug of poly(A)+ mRNA from *A. nigulans* was used for construction of a cDNA pool in plasmid pYcDE8 as described by McKnight et al. (*EMBO J.* 4: 2093–2099, 1985). 80,000 ampicillin resistant *E. coli* colonies were recovered and plasmid DNA was prepared and purified by CsCl gradient centrifugation.

*S. cerevisiae* strain Δtpi29(a Tpi⁻ derivative of strain E2-7B [ATCC# 20689] produced by disrupting the TPI1 gene according to the method of Rothstein [*Meth. in Enzymology* 101: 202–210, 1983] using the *S. cerevisiae* LEU2 gene inserted into the TPI1 gene [Alber and Kawasaki, *J. Mol. Appl. Genet.* 1: 419–434, 1982] (as described in co-pending, commonly assigned U.S. Ser. No. 734,119, which is incorporated herein by reference in its entirety) was transformed with the cDNA library and the cells plated on dextrose-sorbitol minimal medium lacking tryptophan to select for transformants producing triose phosphate isomerase. A total of 46 such Tpi+ colonies were obtained. Plasmid DNA was prepared (*BRL Focus* 6: 11, 1984) from 12 of these transformants and each plasmid sample was used to transform *E. coli* MC1061 to ampicillin resistance. Following analysis of plasmid DNA, 6 of the original 12 plasmids were found to have a common cDNA insert size of approximately 1150 bp. Plasmid DNA from one transformant was digested with EcoRI and BamHI and the tpiA cDNA fragment was subcloned into EcoRI+BamHI digested pUC19 (Norrander etal., *Gene* 26: 101–106, 1983).

B. Cloning of *A. nidulans* tpiA gene

The EcoRI+BamHI cDNA fragment was nicktranslated and used to probe an *A. nidulans* genomic DNA library in bacteriophage λ (McKnight et al., ibid). Phage DNA was prepared from positive plaques (Maniatis et al., *Molecular Cloning: A Laboratory Manual,* Cold Spring Harbor Laboratory, 1982). The DNA was digested with various restriction enzymes and probed with the labelled cDNA.

A ~20 kb EcoRI insert from a positive λ clone was inserted into the EcoRI site of pUC19 to construct plasmid pM099. *E. coli* JM83 transformed with pM099 has been deposited with the ATCC under accession number 53430. A ~4 kb HindIII fragment from pM099 was subcloned into the HindIII site of pUC19 to construct plasmid pM100 (FIG. 2). Similarly, a 900 bp SstI fragment was used to construct plasmids pM101 and pM 102.

The 4 kb HindIII fragment and the 900 bp SstI fragment were also inserted into M13mp18 and sequenced. The M13 clone containing the 900 bp insert was designated S4 (FIG. 2). The tpiA cDNA was also sequenced. FIG. 1 shows the sequence of a portion of the tpiA genomic clone comprising the coding region. The 5' end of the tpiA cDNA is at nucleotide 232 and the polyadenylation site is at nucleotides 1647–1648.

C. Construction of *A. nidulans* tpiA Promoter Fragment

Figure 3:
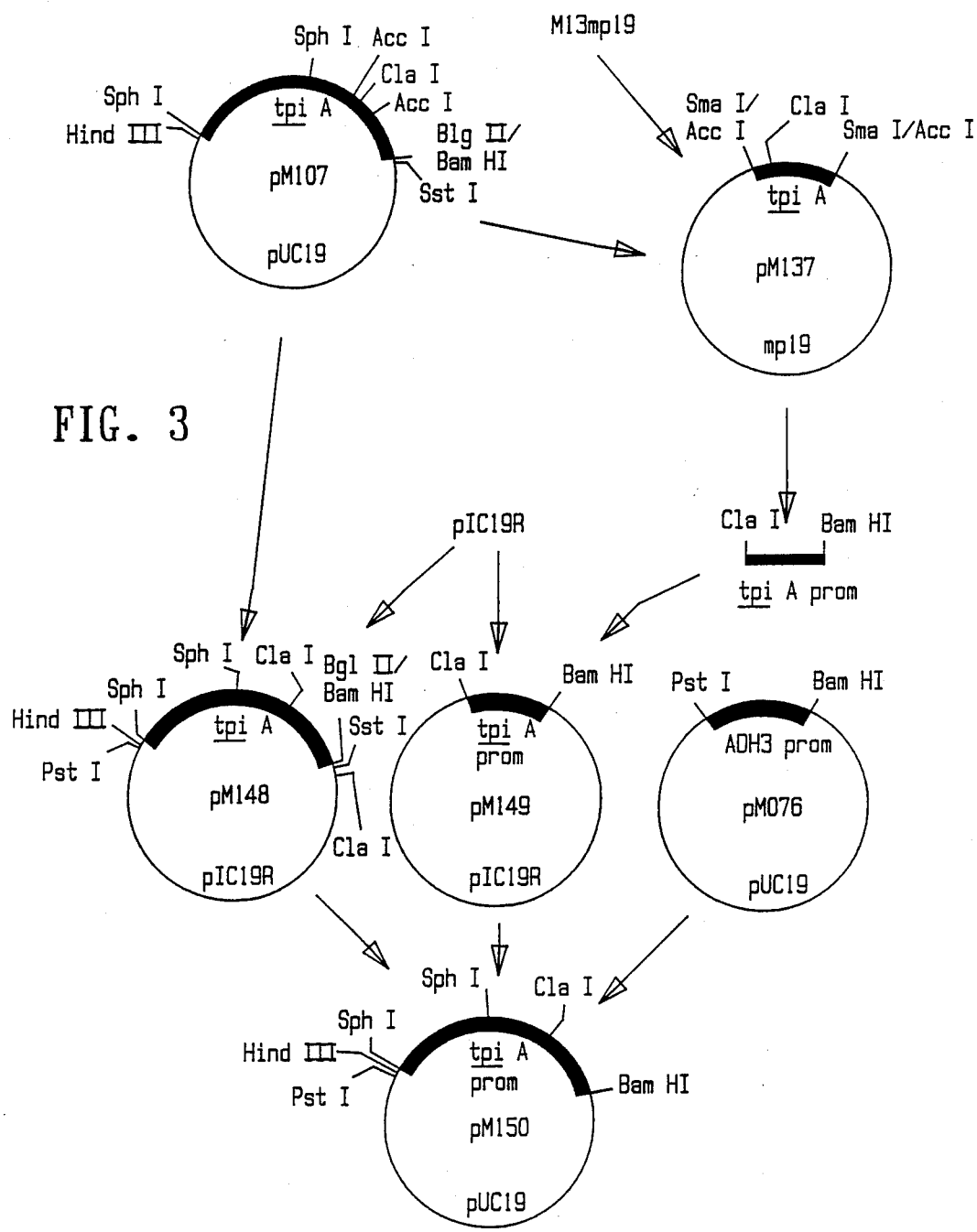
FIG. 3 illustrates the construction of an interchangeable tpiA promoter.

The construction of an interchangeable tpiA promoter fragment involved the placement of BamHI and EcoRI sites adjacent to and upstream of the natural initiator ATG of the tpiA gene. Plasmid pM100 was digested to completion with BglII and partially digested with SphI. A ~2 kb fragment comprising the promoter and 5' non-coding region was subcloned in SphI+BamHI digested pUC19 to construct the plasmid pM107 (FIG. 2). Referring to FIG. 3, a 273 bp AccI fragment was prepared from pM107, blunt-ended by the Klenow fragment of DNA Polymerase I and inserted into the phosphatased SmaI site of M13mp19. The orientation of the inserts was determined by DNA sequencing and a phage clone having the insert in the desired orientation was designated pM137. To modify the promoter sequence, the pM137 template DNA was annealed with oligonucleotide ZC761 (5'TTG AGT GTC TAG TTG TGT AT3') and DNA was synthesized by the Klenow fragment of *E. coli* DNA Polymerase I in the presence of nucleotide triphosphates. The reaction mixture was denatured, annealed with New England Biolabs M13 Reverse Sequencing Primer (5'AAC AGC TAT GAC CAT G3') and second strand DNA was synthesized by the Klenow fragment in the presence of all four nucleotide triphosphates. A DNA fragment of approximately 190 bp containing a blunt-end corresponding to the position of oligonucleotide ZC761 was prepared by PstI digestion and gel purification. Phosphorylated BamHI linkers (5'CGG ATC CG3', obtained from PL Biochemicals) were ligated to the blunt-end of the DNA fragment. The reaction mixture was digested with ClaI and Bam HI and the resultant ClaI-BamHI fragment was gel purified and inserted into ClaI+BamHI digested pIC19R to produce pM149. Plasmid pM107 was digested with HindIII and SstI and the kp DNA fragment was gel purified and inserted into HindIII+SstI digested pIC19R to produce pM148. The promoter fragment was regenerated by ligating the 1.5 kp PstI-ClaI fragment of pM148 with the ClaI-BamHI fragment of pM149 in the ~2.7 kp PstI-BamHI fragment of pM076 (Example 3A). The resulting plasmid was designated pM150 (FIG. 3). The BamHI linker was shown to be located 4 nucleotides upstream of the initiator ATG of tpiA.

D. Cloning of A. nidulans tpiA Terminator Fragment

Referring to FIG. 2, the 3' non-coding and polyadenylation sequences were isolated from the M13 clone S4 by hybridization with oligonucleotide ZC607(5'CTC GCA AAA GCT TAC AGG CGG GC3') and subsequent digestion with HindIII in order to obtain a fragment having an internal HindIII site. The reaction mixture was then annealed with the Amersham oligonucleotide N4511 (5'GTA AAA CGA CGG CCA GT3') and DNA was synthesized by the Klenow fragment of E. coli DNA polymerase I in the presence of nucleotide triphosphates. The reaction mixture was digested with SstI and blunt-ended by T4 polymerase. The resulting blunt-ended 442 bp fragment, which contains 3' noncoding and adjacent downstream DNA, was ligated to the phosphatased HincII site of pUC19. The ligation mixture was transformed into E. coli JM83, ampicillin-resistant colonies were obtained, and white colonies were chosen for plasmid extraction and analysis. Plasmid pMLP100 (FIG. 2) contains a 442 bp fragment in which the blunt-ended HindIII site is adjacent to the XbaI site of pUC19, and the blunt-ended SstI site is adjacent to the PstI site of pUC19. Plasmid pMLP101 contains the same 442 bp fragment in the opposite orientation.

EXAMPLE 2

Isolation of A. niger tpiA and adhA Genes

A. Cloning of A. niger tipA and adhA cDNAs

A soil isolate of *Aspergillus niger* (designated WM32) was used as the source of mRNA in the construction of an A. niger cDNA pool. The A. niger spores were inoculated into flasks containing 400 ml of minimal medium containing 0.5% (w/v) glucose and grown with shaking overnight at 37° C. The hyphae were recovered by filtration through cheesecloth, thoroughly washed with sterile water, and inoculated into fresh minimal medium lacking glucose, but containing 1.0% (v/v) ethanol, and grown with shaking for four hours at 37° C. The hyphae were recovered by filtration through cheesecloth, washed with sterile water, pressed dry and ground in a mortar and pestle in liquid nitrogen.

The powdered hyphae were added to 10 ml of a solution containing 200 mM Tris pH 8.5, 250 mM NaCl, 50 mM EGTA, 4.8% (w/v) para-amino salicylate, 0.80% (w/v) triisopropyl napthalene sulfonate to which was added 5 ml of phenol (saturated with 10 mM Tris pH 7.5, 1 mM EDTA) and 5 ml of chloroform. The suspension was vortexed, centrifuged and the soluble supernatant was stored on ice in 3 ml phenol while the interface was re-extracted with 2 ml of the solution described above by heating to 65° C. for 10'. The soluble supernatants were combined and extracted three times with 50% (v/v) phenol, 49% (v/v) chloroform and 1% (v/v) isoamyl alcohol previously saturated with 10 mM Tris pH 7.5, 1 mM EDTA. The aqueous phase was precipitated with 1/10 volume of 3M NaOAC pH 5.2 and 2 volumes of 100% ethanol and stored at −80° C. for 1½ hours. The nucleic acid was pelleted, washed with 75% ethanol, dried and resuspended in distilled sterile water. Poly(A)+ RNA was purified by two cycles of binding to and elution from oligo(dT) cellulose.

A cDNA pool in plasmid pYcDE8 was prepared from 6 ug of the A. niger poly(A)+ RNA. Approximately 60,000 transformants of E. coli MC1061 (for example, McKnight et al., ibid) were obtained.

Plasmid DNA was extracted and purified by CsCl gradient centrifugation. S. cerevisiae strain 500-11 (Adh−) was transformed with the A. niger cDNA pool, plated on sorbitol dextrose medium lacking tryptophan and incubated at 30° C. After two days of growth, the plates were each overlayed with 50 ug of antimycin A in agar and incubated at 30° C. Adh+ colonies were then picked onto dextrose medium lacking tryptophan.

S. cerevisiae strain Δtpi29 was also transformed with the A. niger cDNA pool, and the cells were plated on sorbitol dextrose medium lacking tryptophan, and incubated at 30° C. Tpi+ colonies were then picked onto dextrose medium lacking tryptophan. Plasmid DNA was extracted from the Adh+ Trp+ and the Tpi+ yeast cells as described above. E. coli RR1 was transformed with the yeast plasmid DNAs and ampicillin-resistant colonies obtained. Plasmid DNA was extracted from the E. coli transformants, digested with EcoRI and BamHI and analyzed by agarose gel electrophoresis. Ten-independent Adh+ yeast colonies each contained an apparently identical cDNA insert approximately 1.5 kb in length. Five independent Tpi+ yeast colonies each contained an apparently identical cDNA insert approximately 1.1 kb in length. The intact adhA and tpiA cDNAs were recovered by EcoRI and XmaI digestion and subcloned into the EcoRI and XmaI sites of pUC19. The A. niger adhA cDNA in pUC19 was designated pM098. The A. niger tpiA cDNA in pUC19 was designated pM095. E. coli strain JM83 transformed with plasmid pM098 has been deposited with the ATCC under accession number 53428.

B. Isolation of A. niger adhA Gene

An *Aspergillus niger* genomic library was prepared in bacteriophage λ. Five 400 ml cultures of A. niger strain WM32 were grown overnight in minimal medium at 37° C. with vigorous shaking. The mycelia were harvested by filtration, washed with cold water, frozen in liquid nitrogen and ground to a fine powder in a pestle and mortar. The powdered mycelia were suspended in 50 ml of buffer (50 mM EDTA, 1% SDS, 20 mM Tris pH 7.5) and incubated at 65° C. for 30 minutes. The suspension was sedimented by centrifugation for 15 minutes in a bench-top centrifuge. The supernatant was transferred to dialysis tubing and buried in PEG 4000 powder to reduce volume. Cesium chloride was added to the concentrated supernatant and the DNA was banded by ultracentrifugation. The DNA was removed from the gradient and the ethidium bromide was extracted with iso-amyl alcohol. Following dialysis against TE (1 mM EDTA, 10 mM Tris pH 7) to remove salts, the DNA was precipitated with ethanol, pelleted, washed in 70% ethanol, dried and resuspended in TE.

The DNA was partially digested with the restriction enzyme Mbo I and fractions were separated on a sucrose gradient. DNA in the size range of 15-20 kilobases was purified. This DNA was ligated to BamHI digested purified arms of the EMBL3 strain of bacteriophage λ (Vector Cloning Systems) and packaged into particles and adsorbed to *E. coli* strain P3292, as directed by the supplier. Adsorbed cells were plated on NZY amine agarose medium and the total phage were collected as a plate lysate in TM buffer (10 mM Tris pH 7.4, 10 mM $MgSO_4$). The lysate was treated with $CHCl_3$, centrifuged and the top phase removed for storage.

A titered sample of the phage library was adsorbed to *E. coli* strain LE392 and plated on NZY amine agarose medium. Plaque lifts to nitrocellulose filters were probed with nick-translated *A. niger* adhA cDNA (Example 2A). Positive plaques were picked and purified through two rounds of plaque purification before analysis. Two positive clones designated λP3 and λQ5 were selected for analysis.

Figure 4:
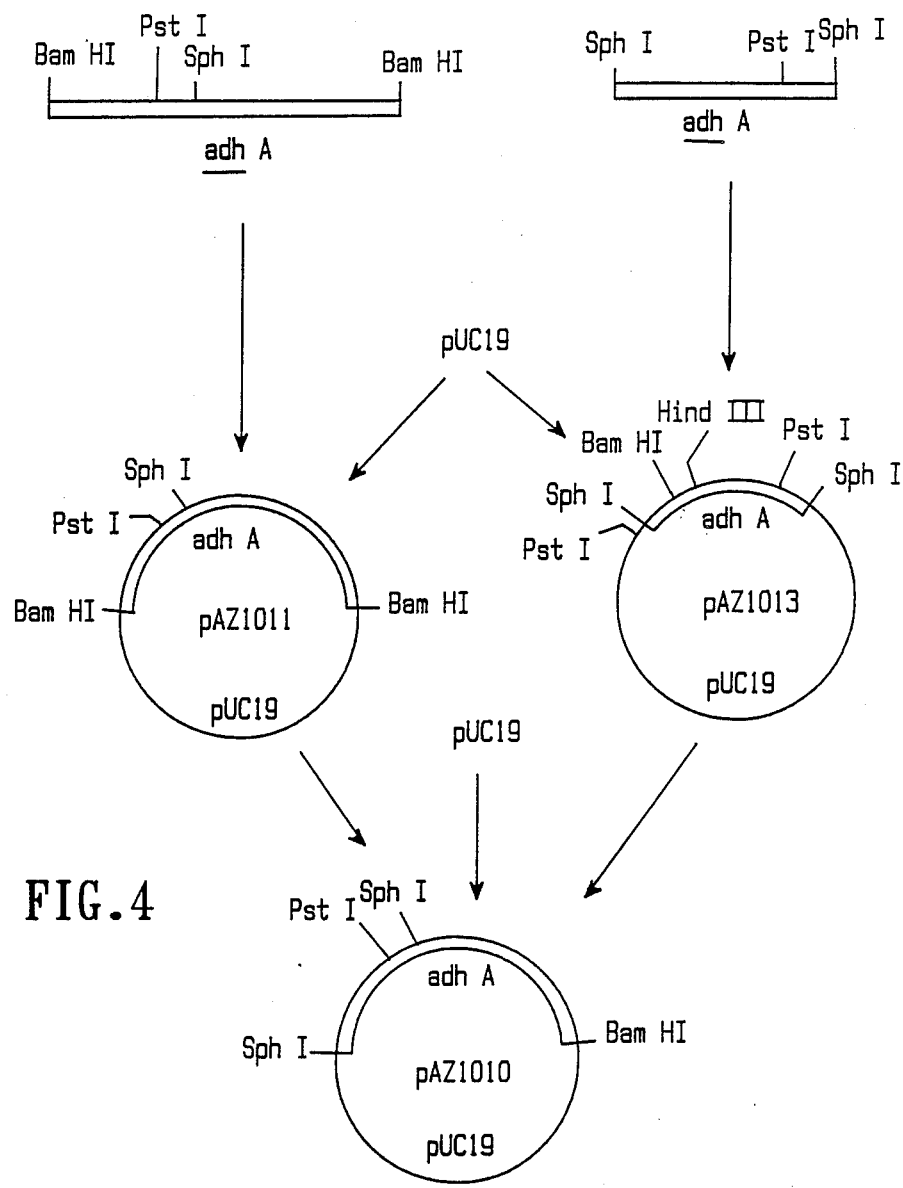
FIG. 4 illustrates the cloning of the *A. niger* adhA gene.

Referring to FIG. 4, portions of the inserts from λP3 and λQ5 were then subcloned and sequenced. λP3 was digested with BamHI and a 3.8 kb fragment containing most of the adhA gene was subcloned into pUC19. The resulting subclone, designated pAZ1011, lacked the promoter and part of the 5' end of the gene. Q5 was digested with Sph I and a 1.8 kb fragment containing the promoter and 5' end of the gene was subcloned into pUC19 to construct pAZ1013. Clone pAZ1011 was digested with PstI and BamHI and a 3.0 kb fragment was isolated. pAZ1013 was digested with SphI and PstI and a 1.5 kb fragment was isolated. These two fragments were mixed with pUC19, which had been digested with SphI and BamHI, in a triple ligation to generate pAZ1010, which contained the complete adhA gene of *A. niger* (FIG. 4). Both the 3.0 and 1.5 kb fragments were also ligated to Sph I+BamHI digested M13mp18 and M13mp19 in triple ligations for subsequent nucleotide sequence analysis. The sequence of the *A. niger* adhA gene is shown in FIG. 5.

C. *Aspergillus niger* adhA Promoter Preparation

Figure 6:
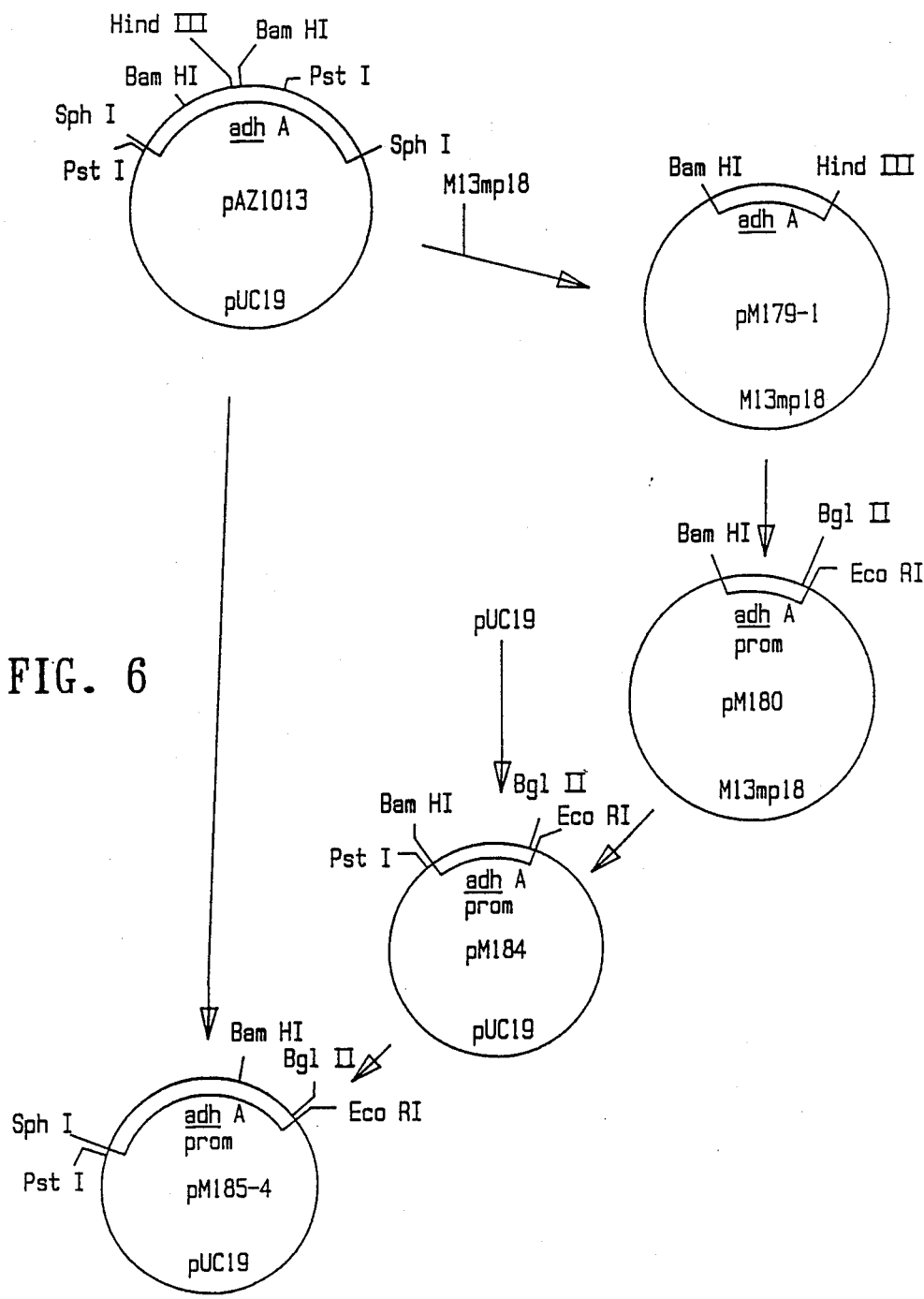
FIG. 6 illustrates the construction of an interchangeable *A. niger* adhA promoter.

The construction of an interchangeable *A. niger* adhA promoter fragment involved the placement of BglII and EcoRI sites adjacent to and upstream of the natural initiator ATG of the adhA gene and is illustrated in FIG. 6. A 424 bp BamHI-HindIII fragment from pAZ1013 (comprising *A. niger* genomic adhA sequence) was ligated into BamHI+HindIII digested M13mp18 to construct pM163T. *E. coli* RZ1032 cells were streaked onto LB-tetracyline (15 ug/ml) plates and grown at 37° C. overnight. Competent cells of RZ1032 were made and tested for infectability with the pM163T template and M13mp11 as control.

Phage preps were then made from the transfected RZ1032 cells. Four plaques were selected and each was added to 1 ml YT. The samples were vortexed and the cells were killed by heating at 60° C. for 5 minutes. Large cultures were prepared by inoculating 100 ml YT.+0.25 ug/ml uridine in 1 liter flasks with 5 ml mid-log RZ1032 cells and 100 ul of the phage samples. These cultures were incubated for 16 hours at 37° C. with shaking. The cultures were then spun and the supernates were collected. The resultant phage preps were designated pM179-1 through pM197-4.

Phage titer comparisons of ung⁻ (RZ1032) and ung⁺ (JM101) *E. coli* hosts were done on the 4 phage preps. The phage titer was determined on each culture by infecting JM101 and RZ1032 with a known amount of phage from the supernates. Phage which contain uracil in the DNA have normal biological activity in ung⁻ (RZ1032) hosts, but greater than $10^5$-fold lower survival in ung⁺ (JM101) hosts. All cultures had uracil-containing DNA and template preparations were made from all four cultures.

Oligonucleotide ZC935 (5'CCA GTG CCA AGC TTG AAT TCA GAT CTA TTG GCA GTC TGG C3') was designed according to the method of Eghtedarzadeh and Henikoff, (*Nuc. Acids Res.* 14: 1986) and used as a mutagenic primer. This oligonucleotide was kinased and annealed to the pM179-1 template. DNA was synthesized by the Klenow fragment of DNA Polymerase I in the presence of nucleotide triphosphates. The resultant mixture was transfected into *E. coli* JM101 (ung+) to allow selection against the uracil-containing template strand. This causes a high percentage of newly mutated (synthesized) strands to be transfected. A control transfection of pM179-1template (uracil-containing DNA) gave no plaques. Six plaques were then picked, phage were used to infect *E. coli* JM 101 and infected cells were grown in 1×YT and template DNA was prepared. The templates were sequenced and four were found to comprise the correctly mutated sequence. These were designated pM180. Replicative form (RF) DNA of pM180 was prepared and cut with BamHI+EcoRI. The cleaved DNA was electrophoresed on an acrylamide gel and the 258 bp fragment was isolated. This 258 pb fragment was ligated into BamHI+EcoRI digested pUC19 and the mixture was transformed into *E. coli* JM83. The resultant plasmid was designated pM184. The 5' adhA promoter fragment was isolated from pAZ1013 as a 0.8 kb PstI-BamHI fragment and was ligated with a 2.9 kb PstI-BamHI fragment of pM184 resulting in the plasmid pM185. Plasmid DNA was prepared and screened for correct insert orientation by restriction enzyme digestion. A plasmic containing the reconstructed adhA promoter was designated pM185-4.

D. Isolation of the *A. niger* tpiA gene

Figure 7:
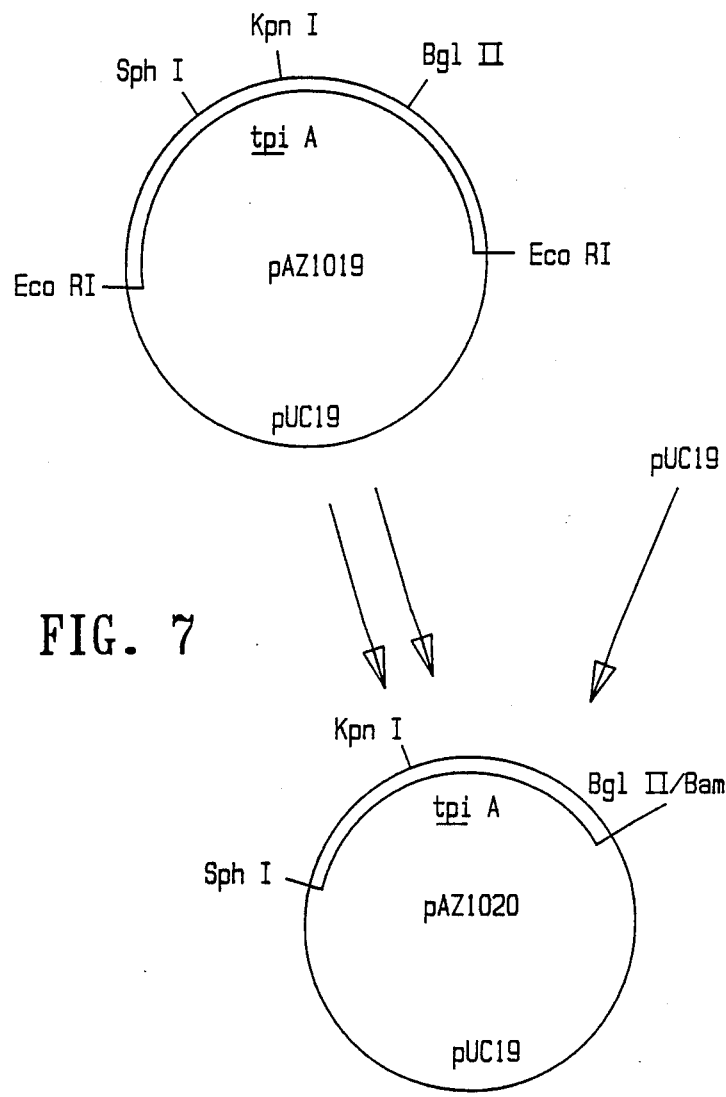
FIG. 7 illustrates the isolation of the *A. niger* tpiA gene.

The *A. niger* tpiA gene was cloned from the λ library described in Example 2B using nick-translated *A. niger* tpiA cDNA as the hybridization probe. A positive clone, designated λRI, was digested with EcoRI and an 8 kb fragment was isolated and subcloned into EcoRI digested pUC19. The resultant plasmid, designated pAZ1019, was subsequently digested with Sph I and Kpn I and a 1.0 kb fragment containing the promoter and 5' end of the gene was isolated. pAZ1019 was also digested with Kpn I and Bgl II and a 1.5 kb fragment containing the 3' end of the gene, including the terminator, was isolated. These two fragments were mixed with Sph I+BamHI digested pUC19 in a triple ligation to generate plasmid pAZ1020 (FIG. 7). The reconstructed gene was excised from pAZ1020 as a 2.5 kb Eco RI-HindIII fragment and was ligated into Eco RI+HindIII digested M13mp18 and M13mp19 for nucleotide sequence analysis. The sequence of the tpiA gene is shown in FIG. 8.

EXAMPLE 3

Construction of t-PA Expression Vectors for Aspergillus

A. Construction of pM090

The sequence of a human t-PA cDNA clone has been reported (Pennica et al., *Nature* 301: 214–221, 1983). The sequence encodes a pre-pro peptide of 32–35 amino acids followed by a 527–530 amino acid mature protein.

A cDNA clone comprising the coding sequence for mature t-PA was constructed, using as starting material mRNA from the Bowes melanoma cell line (Rijken and Collen, *J. Biol. Chem.* 256: 7035–7041, 1981). This cDNA was then used to construct the plasmid pDR1296. *Escherichia coli* strain JM83 transformed with pDR1296 has been deposited with the American Type Culture Collection under Accession No. 53347.

Because the pre-pro sequence was not present in the cDNA clone pDR1296, it was constructed from synthesized oligonucleotides and subsequently joined to the cDNA. Cleavage sites for BamHI and NcoI are present immediately 5' to the first codon (ATG) of the pro-pro sequence, and a BglII (Sau3A, XhoII) site is located at the 3' end. The naturally occurring pre-pro sequence lacks a convenient restriction site near the middle; however, the sequence GGAGCA (coding for amino acids −20 and −19, Gly-Ala) can be altered to GGCGCC to provide HaeIII and NarI sites without changing the amino acid sequence.

To construct the pre-pro sequence, the following oligonucleotides were synthesized using an Applied Biosystems Model 380-A DNA synthesizer:

| | |
|---|---|
| ZC131: | 5'GGA TCC ATG GAT GCA ATG AAG AGA GGG CTC TGC TGT GTG3' |
| ZC132: | 5'TGG CGC CAC ACA GCA GCA GCA CAC AGC AGAG3' |
| ZC133: | 5'GGC GCC GTC TTC GTT TCG CCC AGC CAG GAA ATC CATG3' |
| ZC134: | 5'AGA TCT GGC TCC TCT TCT GAA TCG GGC ATG GAT TTC CT3' |

Following purification by polyacrylamide gel electrophoresis on denaturing gels, oligomers ZC131 and ZC132 were annealed to produce an overlap of 12 base pairs (Section 1). Oligomers ZC133 and ZC134 were similarly annealed (Section 2).

The oligomers were mixed in Pol I buffer (Bethesda Research Labs), heated to 65° C. for five minutes, and slowly cooled to room temperature for four hours to anneal. Ten units of DNA polymerase I were added and the reaction proceeded for two hours at room temperature. The mixtures were electrophoresed on an 8% polyacrylamide-urea sequencing gel at 1,000 volts for 2½ hours in order to size fractionate the reaction products. The correct size fragments (those in which the polymerase reaction went to completion) were cut from the gel and extracted.

After annealing, Section 1 was cut with BamHI and NarI and cloned into BamHI+NarI-cut pUC8 (Vieira and Messing, *Gene* 19: 259–268, 1982; and Messing, *Methods in Enzymology* 101: 20–77, 1983). Section 2 was reannealed and cut with NarI and BglII and cloned into BamHI+NarI-cut pUC8. Colonies were screened with appropriate labelled oligonucleotides. Plasmids identified as positive by colony hydridization were sequenced to verify that the correct sequence had been cloned.

Section 1 was then purified from a BamHI+NarI double digest of the appropriate pUC clone. Section 2 was purified from a NarI+XhoII digest. The two fragments were joined at the NarI site and cloned into BamHI-cut pUC8.

Figure 9:
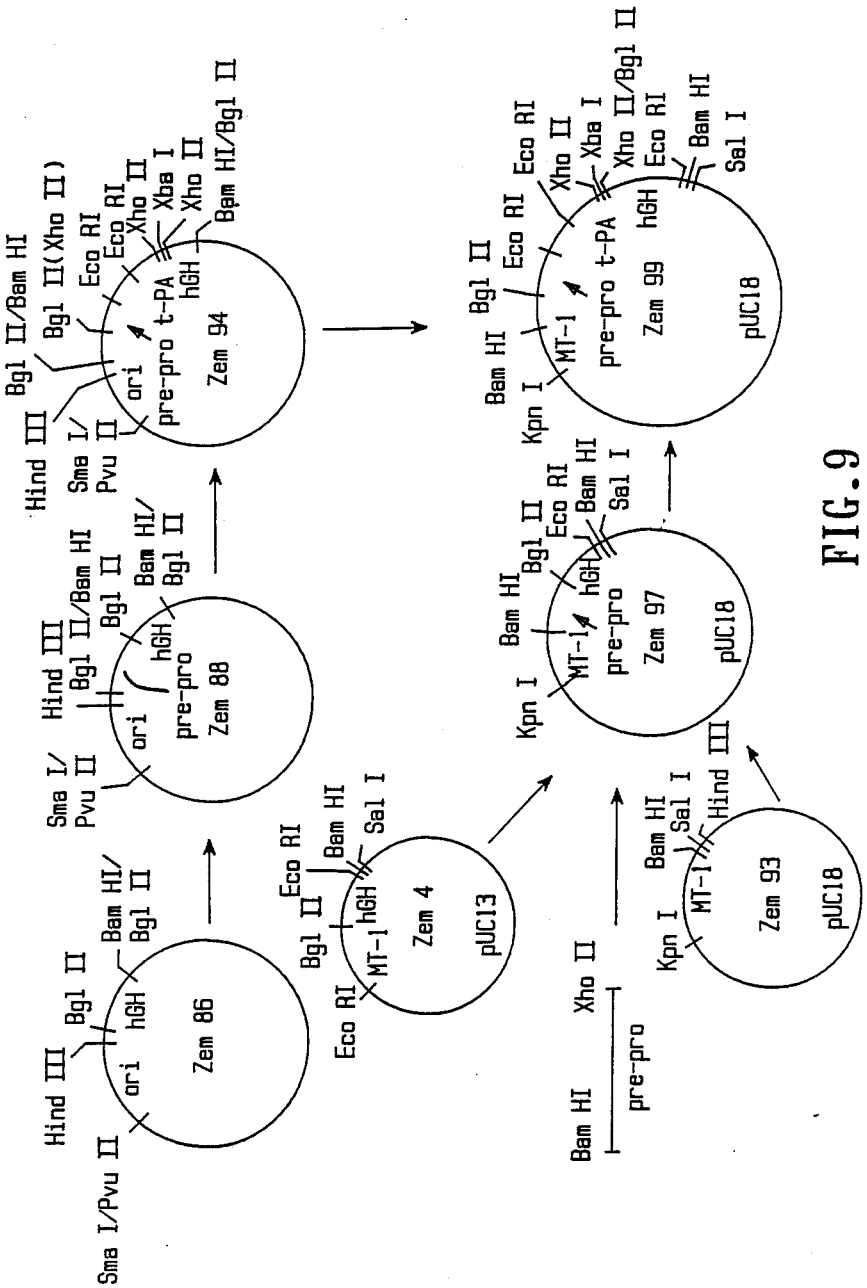
FIG. 9 illustrates the construction of the plasmid Zem99.

The t-PA sequence of pDR1296 was then joined to the synthesized signal sequence in the following manner (FIG. 9). Plasmid pIC19R (Marsh et al., *Gene* 32: 481–486, 1984) was digested with SmaI and HindIII. The ori region of SV40 from map position 270 (PvuII) to position 5171 (HindIII) was then ligated to the linearized pIC19R to produce plasmid Zem67. This plasmid was then cleaved with BglII and the terminator region from the human growth hormone gene (de Noto et al., *Nuc. Acids Res.* 9: 3719–3730, 1981) was inserted as a BglII-BamHI fragment to produce plasmid Zem86. The synthesized t-PA pre-pro sequence was removed from the pUC8 vector by digestion with Sau3A. This fragment was inserted into BglII-digested Zem86 to produce plasmid Zem88. Plasmid pDR1296 was digested with BglII and BamHI and the t-PA cDNA fragment was isolated and inserted into BglII-cut Zem88. The resultant plasmid was designated Zem94.

The vector Zem99, comprising the MT-1 promoter, complete t-PA coding sequence, and the hGH terminator, was then assembled in the following manner (FIG. 9). A KpnI-BamHI fragment comprising the MT-1 promoter was isolated from MThGH111 (Palmiter et al., *Science* 222: 809–814, 1983) and inserted into pUC18 to construct Zem93. Plasmid MThGH112 (Palmiter et al., ibid.) was digested with BglII and religated to eliminate the hGH coding sequence. The MT-1 promoter and hGH terminator were then isolated as an EcoRI fragment and inserted into pUC13 to construct Zem4.

Zem93 was then linearized by digestion with BamHI and SalI. Zem4 was digested with BglII and SalI and the hGH terminator was purified. The t-PA pre-pro sequence was removed from the pUC8 vector as a BamHI-XhoII fragment. The three DNA fragments were then joined and a plasmid having the structure of Zem97 (FIG. 9) was selected. The t-PA fragment from Zem94 was isolated by partial digestion with XhoII and inserted into BglII cut Zem97. The resultant vector is Zem99.

Figure 10:
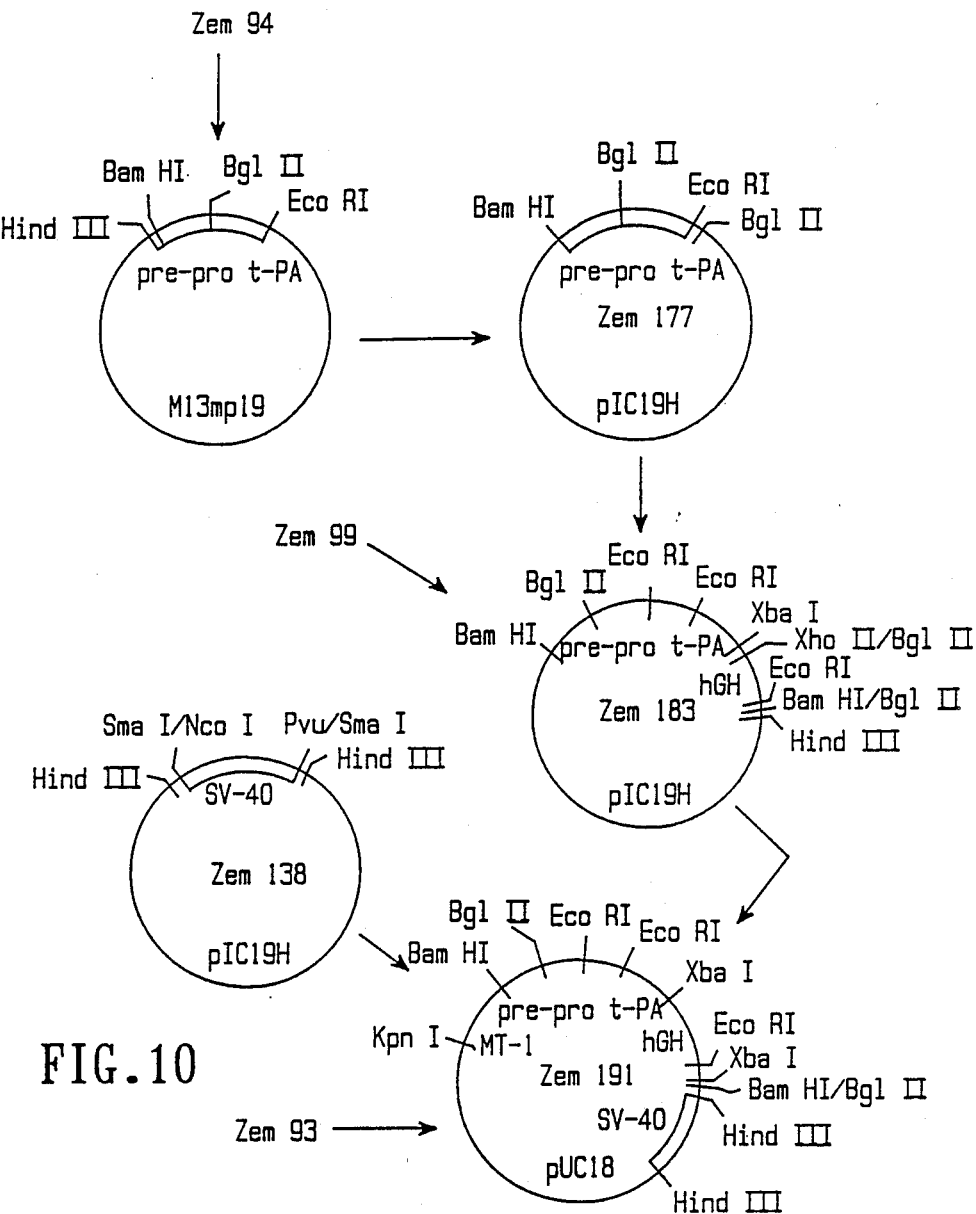
FIG. 10 illustrates the construction of the plasmid Zem 191.

The sequence just upstream of the ATG start codon of the t-PA sequence in Zem94 was altered by site-specific mutagenesis resulting in the positioning of HindIII and BamHI sites adjacent to the ATG (FIG. 10). The resultant nucleotide sequence contains an adenine in the −3 position, which is the most commonly occurring nucleotide in this position in Aspergillus. Single stranded M13 template DNA was prepared by inserting a ~800 bp HindIII-EcoRI fragment from Zem94 comprising polylinker, pre-pro, and a portion of the mature t-PA sequences into M13mp19. Site-specific mutagenesis was carried out essentially as described by Zoller, et al. (*Manual for Advanced Techniques in Molecular Cloning Course*, Cold Spring Harbor Laboratory, 1983), using the oligonucleotide ZC444 (5'CAT CCA TGG TGG ATC CAA GCT TGG C3') as mutagenic primer. Oligonucleotide ZC87 was used as second primer. The mutated inserts were sequenced by the dideoxy method, and a clone in which polylinker sequences had been deleted and the BamHI site at the 5' end of the pre-pro sequence had been restored was selected. This phage clone was digested with BamHI and EcoRI and the t-PA sequence cloned into BamHI+EcoRI digested pIC19H (Marsh et al., ibid.) to generate plasmid Zem177. Zem177 was digested with BglII and the BglII-BamHI fragment from Zem99 comprising the bulk of the cDNA molecule and the complete hGH terminator fragment was inserted. The resultant plasmid was designated Zem183. The SV40 enhancer sequence was inserted into SmaI-digested pIC19H as a blunted NcoI-PvuII fragment to construct Zem138. The SV40 enhancer was then removed from Zem138 as a HindIII fragment and ligated to the BamHI-HindIII fragment of Zem183 and BamHI+HindIII cut Zem93. The resulting plasmid was designated Zem191 (FIG. 10).

Figure 11:
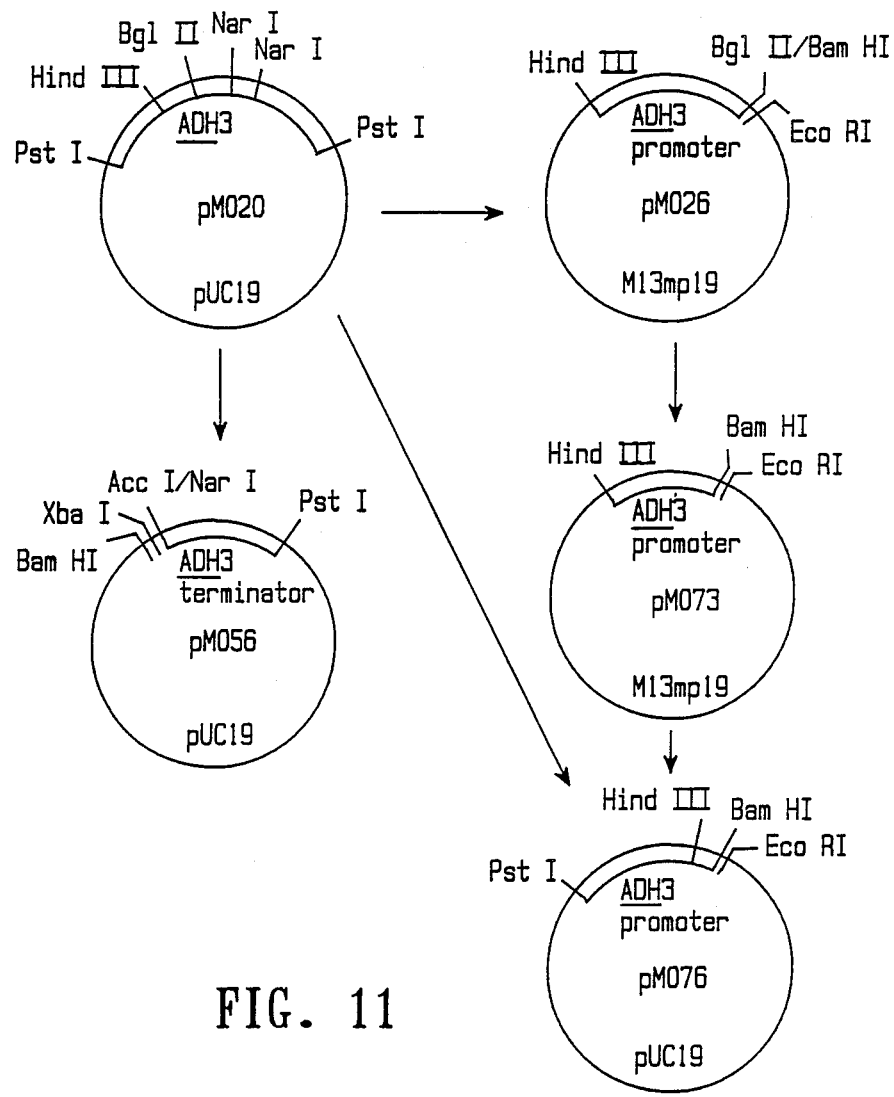
FIG. 11 illustrates the subcloning of the *A. nidulans* ADH3 promoter and terminator.

Referring to FIG. 11, the ADH3 promoter and terminator were subcloned from a 3.4 kb PstI *Aspergillus nidulans* genomic DNA fragment comprising the ADH3 gene, which was inserted into the PstI site of pUC19 to construct pM020 (McKnight, et al., *EMBO J.* 4: 2093–2099, 1985). Site-specific mutagenesis was used to alter the sequence at the initiator ATG to comprise BamHI and EcoRI sites and to delete a portion of the polylinker. The 233 bp HindIII-BglII fragment of pM020 was ligated into the HindIII-BamHI sites of M13mp19 and designated pM026. Single stranded M13 DNA from pM026 was annealed to the kinased mutagenic oligonucleotide ZC341 (5'AGT GAA TTC GGA TCC TTG GGA TGA GAG3') and the oligonucleotide primer ZC87 (5'TCC CAG TCA CGA CGT3') and extended by the large fragment of *E. coli* PolI. The reaction mixture was transfected into competent *E. coli* JM101, and the resulting plaques were tested for hybridization to $^{32}$P-kinase-labelled ZC341. Positive plaques were picked and designated pM073, and the M13 phage were propagated in *E. coli* JM101. M13 replicative form (RF) DNA was prepared and a 100 bp HindIII-EcoRI fragment was excised, gel purified, ligated to the PstI-HindIII 1.0 kb fragment of pM020 and to PstI+EcoRI digested pUC19. The resultant plasmid, designated pM076, contains the ADH3 promoter and 5' non-coding region with BamHI and EcoRI sites located in place of the ADH3 initiator ATG codon. The sequence of the modified promoter fragment is shown in FIG. 12. The downstream portion of pM020, comprising a 1 kb NarI-PstI fragment, was ligated to the AccI-PstI sites of pUC19 and designated pM056. This fragment encompasses intervening sequence B, the 3' non-coding region and polyadenylation site of ADH3.

Figure 13:
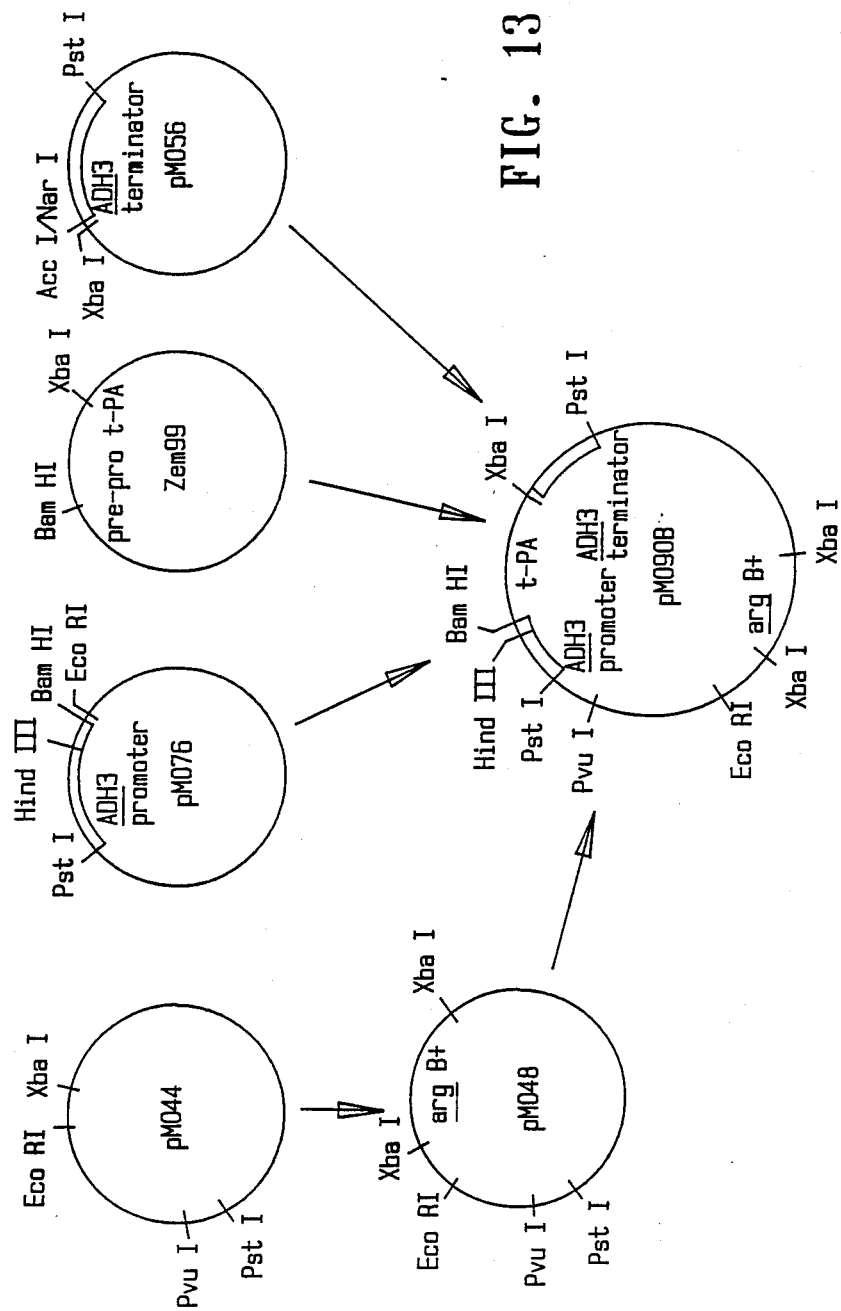
FIG. 13 illustrates the construction of expression vector pM090B.

The XabI-PstI fragment from pM056 was used in the construction of pM090 (FIG. 13). The vector used was based on plasmid pBR329 (Covarrubias and Bolivar, *Gene* 17: 79–89, 1982) which was altered by conversion of the PvuII site to an XbaI site by linker addition and designated pM044. A 3.4 kb XabI fragment encompassing the argB+ gene of *A. nidulans* (Berse et al., *Gene* 25: 107–117, 1983) was inserted into the XabI site of pM044 and the resulting plasmid designated pM048. The BamHI-XbaI fragment from Zem99, containing the cDNA for human tissue plasminogen activator (tPA), the PstI-BamHI fragment of pM076, and the XbaI-PstI fragment of pM056 were joined, in a four part ligation, to the phosphatased PstI-digested pM048. The resultant plasmid was designated pM090. *E. coli* transformants containing pM090 were selected for resistance to tetracycline and screened for ampicillin sensitivity. The composite PstI fragment containing the expression unit could be inserted in either of two orientations in the vector. The pM090 *E. coli* transformants were characterized with regard to orientation and pM090B was chosen for transformation of *A. nidulans*.

B. Construction of Additional t-PA Expression Vectors

Figure 14:
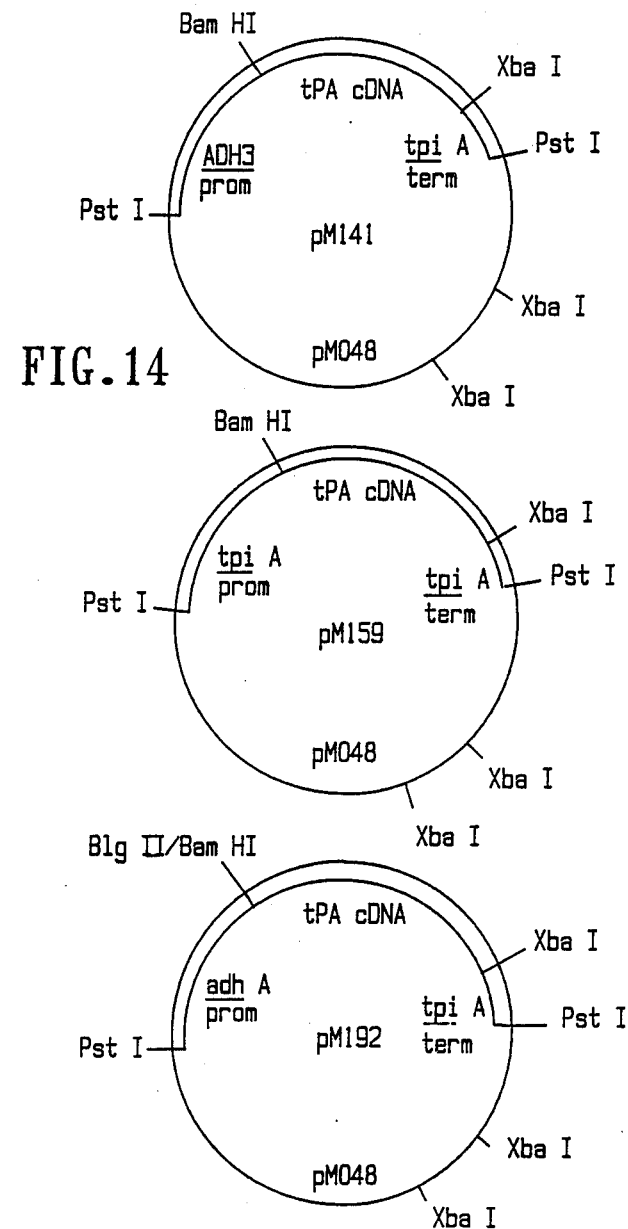
FIG. 14 shows partial restriction maps of the plasmids pM141, pM159, and pM192.

The BamHI-XbaI fragment from Zem99, containing the cDNA for human t-PA, was inserted into the BamHI and XbaI sites of pUC19, and the resultant plasmid was designated pM091. The BamHI-XbaI fragment of pM091 is then used in constructing the vectors pM141, pM159 and pM192, shown in FIG. 14.

The PstI-BamHI ADH3 promoter fragment from pM076, the BamHI-XbaI t-PA cDNA from pM091 and the XabI-PstI tpiA terminator fragment from pMLP100 were joined in a four part ligation to phosphate, PstI-digested pM048. The resultant plasmid was designated pM141. *E. coli* RR1 was transformed with pM141. Transformants were selected on the basis of resistance to tetracycline and were screened for ampicillin sensitivity.

The PstI-BamHI tpiA promoter fragment from pM150, the BamHI-XbaI t-PA cDNA from pM091 and the XbaI-PstI tpiA terminator fragment of pMLP100 were joined in a four part ligation to phosphatased, PstI-digested pM048. The resultant plasmid was designated pM159. *E. coli* JM83 was transformed with pM159 and transformants were selected for resistance to tetracycline and were screened for sensitivity to ampicillin. The orientation of the composite PstI fragment containing the expression unit in pM159 was then determined.

The BamHI-XbaI t-PA fragment from pM091, the PstI-BglII adhA promoter fragment from pM185-4 and the tpiA terminator fragment from pMLP100 are joined in a four part ligation with phosphatased, PstI-digested pM048. The resultant plasmid is designated pM192. *E. coli* JM83 cells containing pM192 are selected on the basis of resistance to tetracycline and screened for sensitivity to ampicillin. The orientation of the composite PstI fragment containing the expression unit is determined by restriction enzyme analysis.

Figure 15:
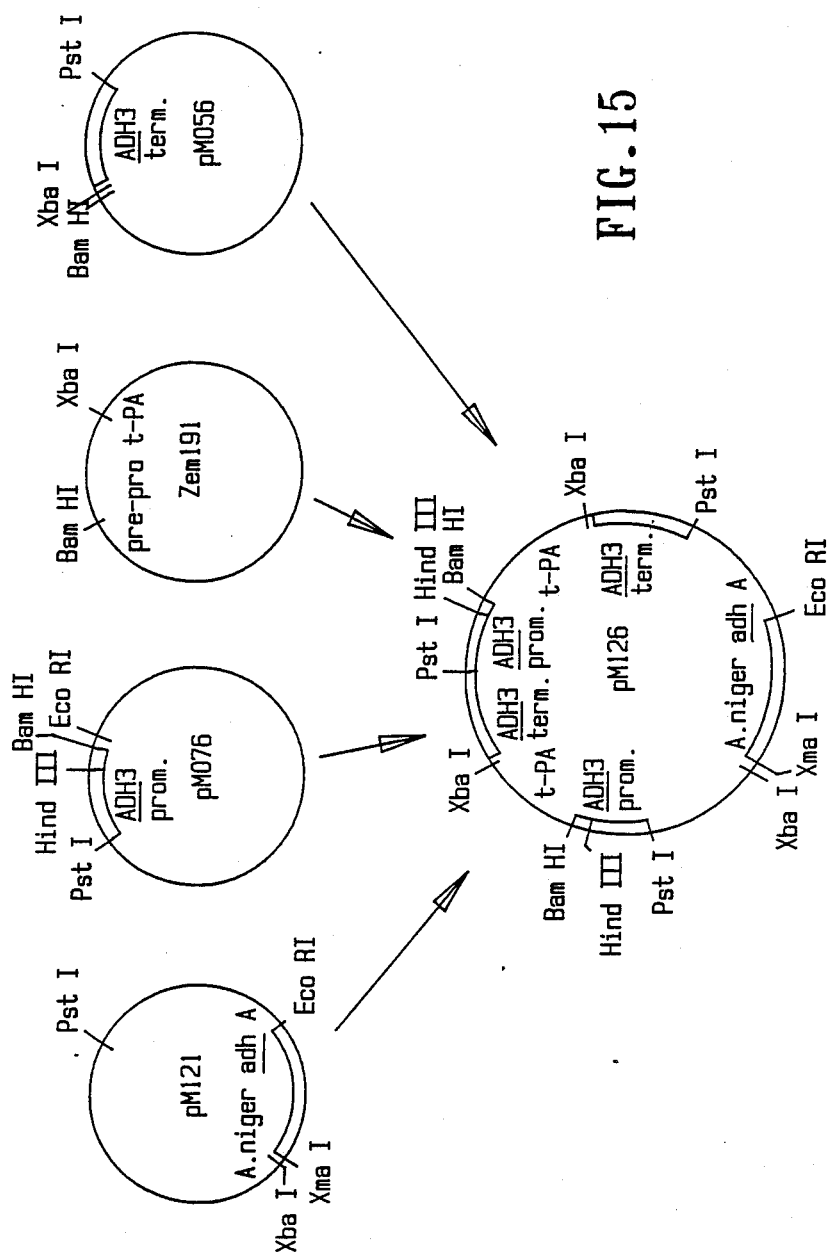
FIG. 15 illustrates the construction of expression vector pM126.

Two additional t-PA expression vectors for use in Aspergillus species, such as *A. niger*, were constructed. Expression vector pM126 contains two copies of the t-PA expression unit in tandem, together with the *A. niger* adhA cDNA, which promotes chromosomal integration. Because it lacks a selectable marker, pM126 must be cotransformed into host cells with a plasmid carrying a selectable marker, such as pM125, which contains the *A. nidulans* amdS gene. Expression vector pM129 contains the t-PA expression unit, the *A. niger* tpiA cDNA, and the *A. nidulans* amdS gene.

pM048 was digested with XbaI and EcoRI and the 4.0 kb pBR329 portion was recovered. The *A. niger* adhA cDNA from pM098 was excised by XbaI and EcoRI digestion, ligated to the XbaI-EcoRI pBR329 fragment from pM048 and designated pM121 (FIG. 15).

pM121 was partially digested with PstI, phosphatased and ligated to the PstI-BamHI ADH3 promoter fragment from pM076, the BamHI-XbaI human t-PA cDNA from Zem191 and the XbaI-PstI ADH3 terminator fragment from pM056. The ligation mixture was transformed into *E. coli* RR1 and tetracycline resistant colonies were obtained. The transformants were tested for sensitivity to ampicillin, the plasmids were then extracted and extensively analyzed by restriction enzyme digestion. Plasmid pM126 contains two copies of the expression unit consisting of the ADH3 promoter, t-PA cDNA and ADH3 terminator in a head-to-tail orientation in pM121 (FIG. 15).

Figure 16:
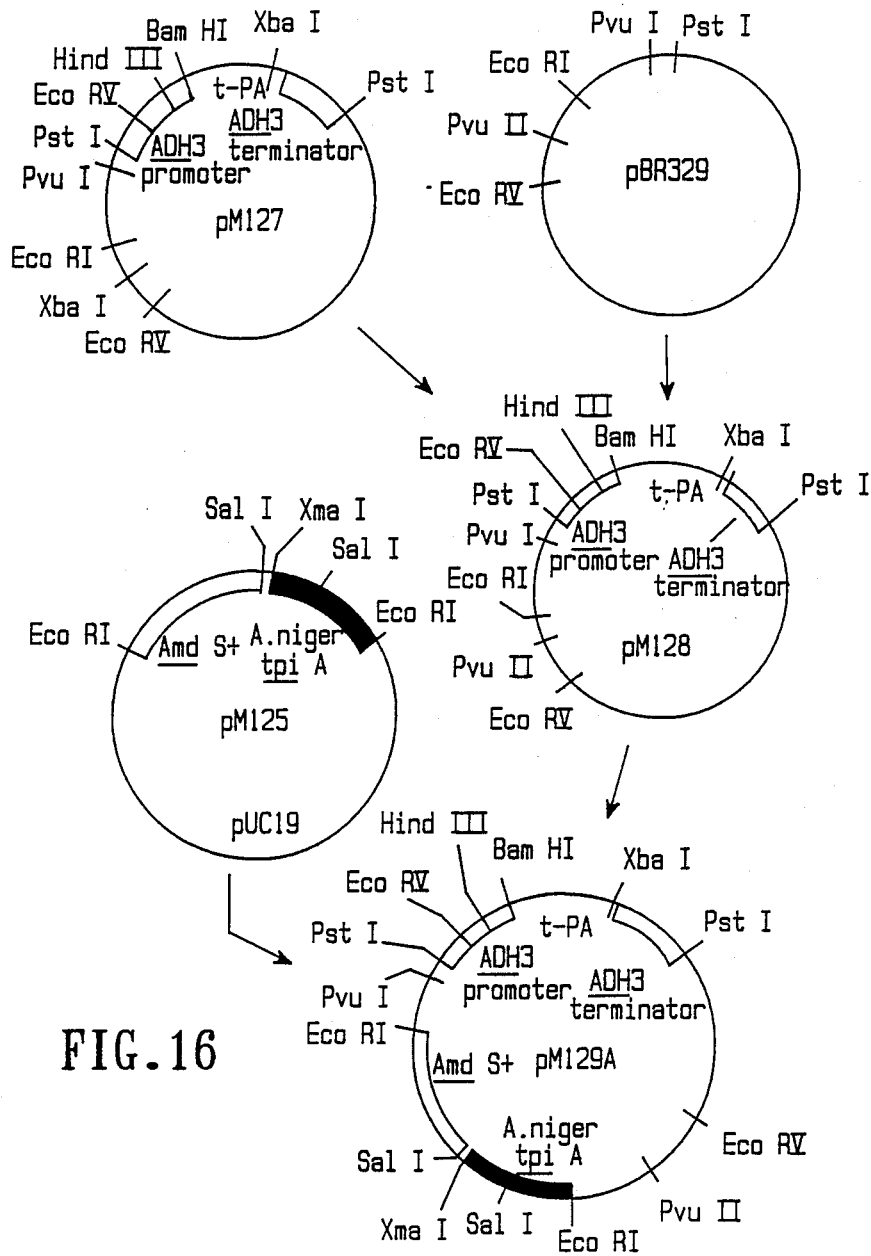
FIG. 16 illustrates the construction of expression vector pM129A.

The *A. niger* tpiA cDNA from pM095 was excised by EcoRI digestion and SalI partial digestion, and ligated to the EcoRI-SalI fragment containing the *A. nidulans* amdS gene from pSR2 (Hynes et al., *Mol. Cell. Biol.* 3: 1430-1439, 1983), and the resulting fragment was ligated to the EcoRI site of pUC19 and designated pM125 (FIG. 16).

Plasmid pM044 was digested with PstI, phosphatased, and ligated to the pM076 PstI-BamHI fragment, the Zem191 BamHI-XbaI t-PA cDNA and the pM056 XbaI-PstI fragment. The resultant plasmid, pM127 (FIG. 16), contains the ADH3 promoter—t-PA cDNA—ADH3 terminator expression unit, but does not confer resistance to chloramphenicol because of the XbaI linker inserted at the PvuII site in pM044. Plasmid pM127 was altered to confer chloramphenicol resistance by digestion with PvuI and partial digestion with EcoRV, recovery of the 6.3 kb fragment and ligation to the 1.7 kb PvuI-EcoRV fragment from pBR329. The ligation reaction mixture was transformed into *E. coli* RR1, chloramphenicol resistant transformants were obtained, the plasmids extracted, characterized and designated pM128 (FIG. 16). Plasmid pM128 was partially digested with EcoRI and the linear (~8 kb) fragment was isolated and ligated to the 6 kb EcoRI fragment from pM125 (FIG. 16), which contains the *A. nidulans* amdS gene and the *A. niger* tpiA cDNA. The ligation mix was transformed into *E. coli* RR1. Tetracycline resistant transformants were obtained, tested for sensitivity to chloramphenicol and the plasmid DNAs were extracted and characterized by restriction enzyme digestion. The plasmid containing the pM125 EcoRI fragment in the pBR329 EcoRI site of pM128 in the orientation shown in FIG. 9 was designated pM129A. *E. coli* RR1 transformed with pM129A has been deposited with the ATCC under accession number 53429.

C. Construction of Expression Vectors Comprising the *A. niger* Glucoamylase Gene Pre-Pro Sequence Plasmid pCAMG91, comprising the *A. niger* glucoamylase genomic DNA fragment inserted into pBR322 (Boel et al. *EMBO J.* 3: 1581-1585, 1984) was digested with EcoRI and SstI, and the 431 bp fragment was isolated and inserted and EcoRI+SstI digested pUC19. The resultant plasmid was designated pM072. The EcoRI-SstI fragment of pM072, comprising the promoter and pre-pro sequence, was digested with AluI and the 258 bp AluI-SstI fragment was isolated. The AluI-SstI fragment was digested with BssHII, blunt-ended with the Klenow fragment of *E. coli* DNA polymerase I in the presence of nucleotide triphosphates, and the resultant 103 bp fragment was isolated and inserted into the EcoRV site of pIC19H to construct pM075-1. The HindII-BamHI fragment of pM075-1, containing the entire glucoamylase pre-pro region, was ligated with the 725 bp BamHI-EcoRI t-PA fragment of pM091 into HindIII+EcoRI digested M13mp19 to construct pM189.

Figure 17A:
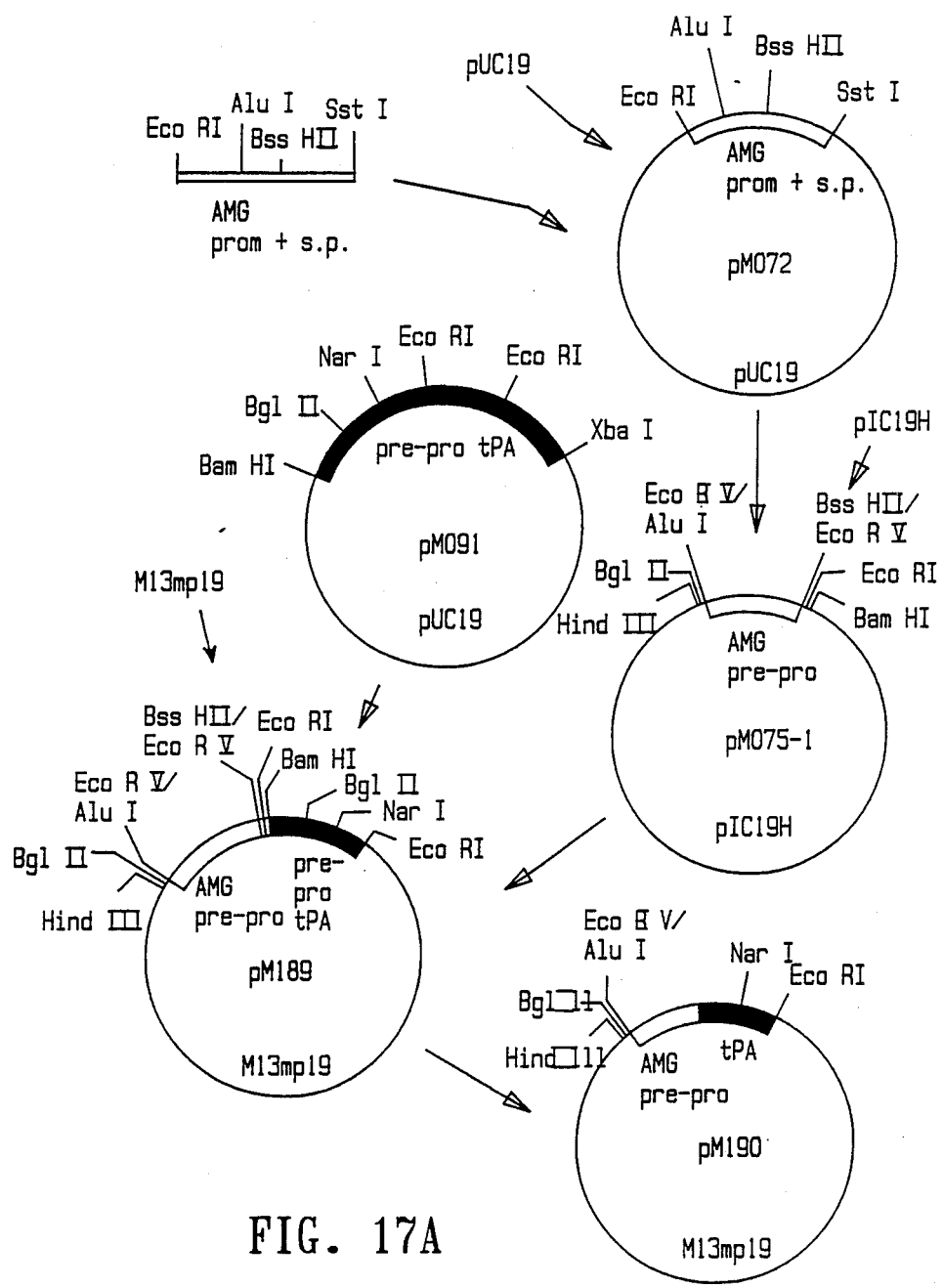
FIGS. 17a through 17c illustrate the construction of vectors containing an expression unit comprising the *A. niger* glucoamylase pre-pro sequence and a human plasminogen activator cDNA. AMG indicates sequences derived from the glucoamylase gene.
Figure 17B:
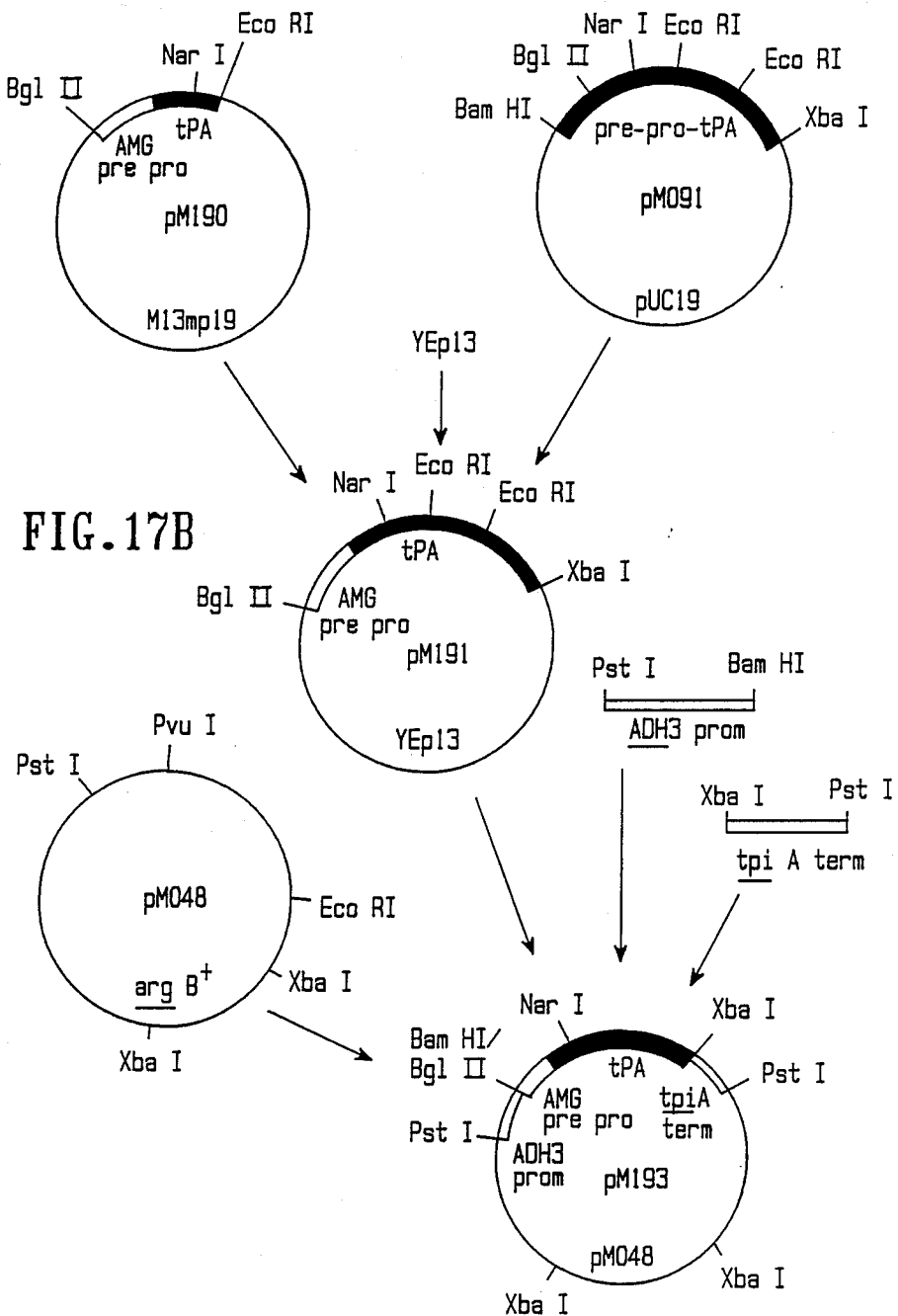

To loop out unwanted 5' t-PA sequences, *E. coli* RZ1032 cells were transfected with pM189 and template DNA was prepared and annealed to the kinased oligonucleotide ZC993 (5' AGA TCA CTT GGT AAG AGC GCT TGG AAA TCA C 3'). DNA was synthesized by the Klenow fragment of *E. coli* DNA polymerase I in the presence of nucleotide triphosphates. This mixture was transfected into *E. coli* JM101 and the desired construction was obtained and designated pM190 (FIG. 17a). The ~440 bp BglII-NarI fragment from pM190 was joined in a triple ligation with the 1.4 kb NarI-XbaI t-PA fragment from pM091 and YEp13 which had been cut with BglII and XbaI. The resultant plasmid was designated pM191. The BglII-XbaI fragment from pM191, the PstI-BamHI ADH3 promoter fragment from pM076 and the XbaI-PstI tpiA terminator fragment from pMLP100 are joined in a four part ligation with phosphatased, PstI-digested pM048. The resultant plasmid is designated pM193 (FIG. 17b).

Figure 17C:
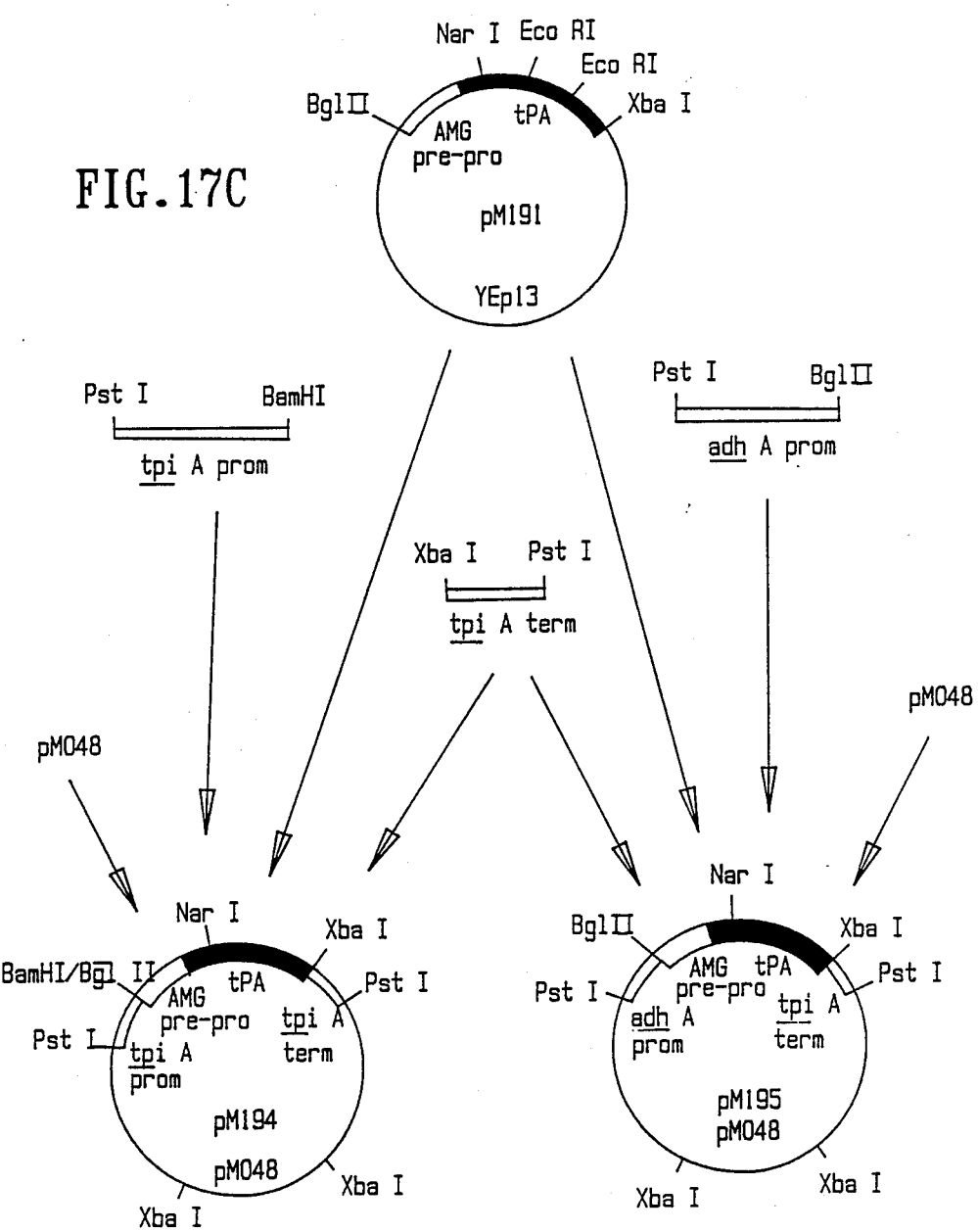

The BglII-XbaI fragment from pM191, the PstI-BamHI tpiA promoter fragment from pM150 and the XbaI-PstI tpiA terminator fragment from pMLP100 are joined in a four part ligation with phosphatased, PstI-digested pM048. The resultant plasmid is designated pM194 (FIG. 17c). The BglII-XbaI fragment from pM191, the PstI-BglII adhA promoter fragment from pM185-4 and the tpiA terminator fragment from pMLP100 are joined in a four part ligation with phosphatased, PstI-digested pM048. The resultant plasmid is designated pM195 (FIG. 17c). *E. coli* JM83 is transformed with pM193, pM194 and pM195 and transformants are selected on the basis of resistance to tetracycline and are screened for sensitivity to ampicillin. The orientations of the composite PstI fragments containing the expression units are determined by restriction enzyme analysis.

EXAMPLE 4

Construction of an IgG Expression Vector for *A. nidulans*

A cDNA encoding a human immunoglobulin heavy chain (IgG) was obtained from a cDNA library constructed from human liver poly A-containing RNA as described by Chandra et al. (*Proc. Natl. Acad. Sci. U.S.A.* 80: 1845-1848, 1983). The cDNA preparation was sedimented through an alkaline sucrose gradient (Monahan, J. J., Harris, S. E., Woo, S. L. C. and O'Malley, B. W. (1976) *Biochemistry* 15: 223-233), and only fractions containing cDNA species of greater than 1,500 nucleotides were pooled. After making the cDNA double stranded enzymatically and treating it with S1 nuclease, the residual staggered ends in the cDNA preparation were filled using the Klenow fragment of DNA polymerase in the presence of all 4 deoxyribonucleoside triphosphates (Maniatis et al., ibid, pp. 97-149). The blunt-ended cDNA was treated with EcoRI methylase prior to ligation with phosphorylated EcoRI linkers using T4 DNA ligase (Maniatis et al., ibid). The ligated DNA preparation was exhaustively digested with EcoRI and double-stranded DNAs greater than 1,500 base pairs in length were obtained by sucrose density gradient centrifugation under non-denaturing conditions, which also removed all the excess EcoRI linkers (Maniatis et al., ibid). The expression phage vector lambda gt11 and *E. coli* host strains Y1088 and Y1090 (Young, R. and Davis, R. *Proc. Natl. Acad. Sci. U.S.A.* 80: 1194, 1983) were used. Native lambda gt11 DNA was ligated into concatemers, digested to completion with EcoRI, and the 5-terminal phosphates were removed by treatment with bacterial alkaline phosphatase. The pooled human liver cDNA was ligated with lambda gt11 DNA and packaged in vitro, as described in Young, R. and Davis, R. ibid. Approximately 14 million phage plaques were generated in this library. Greater than 90% of these are recombinants containing human DNA inserts as suggested by their lack of beta-galactosidase activity and characterization of 20 randomly selected cDNA clones by EcoRI digestion followed by agarose gel electrophoresis. The phage particles were pooled, purified using isopycnic CsCl gradients and stored in TM buffer.

The human liver cDNA library was then screened using protein A essentially as described by Young et al. (*Science* 222: 778–782, 1983) at pH 8.5. A clone which bound protein A was selected and the cDNA insert was removed by digestion with EcoRI and SmaI. This fragment was inserted into EcoRI+HincII-digested pUC13 to produce plasmid pUC835. Sequencing of the insert in pUC835 identified it as an immunoglobulin coding sequence.

Figure 18:
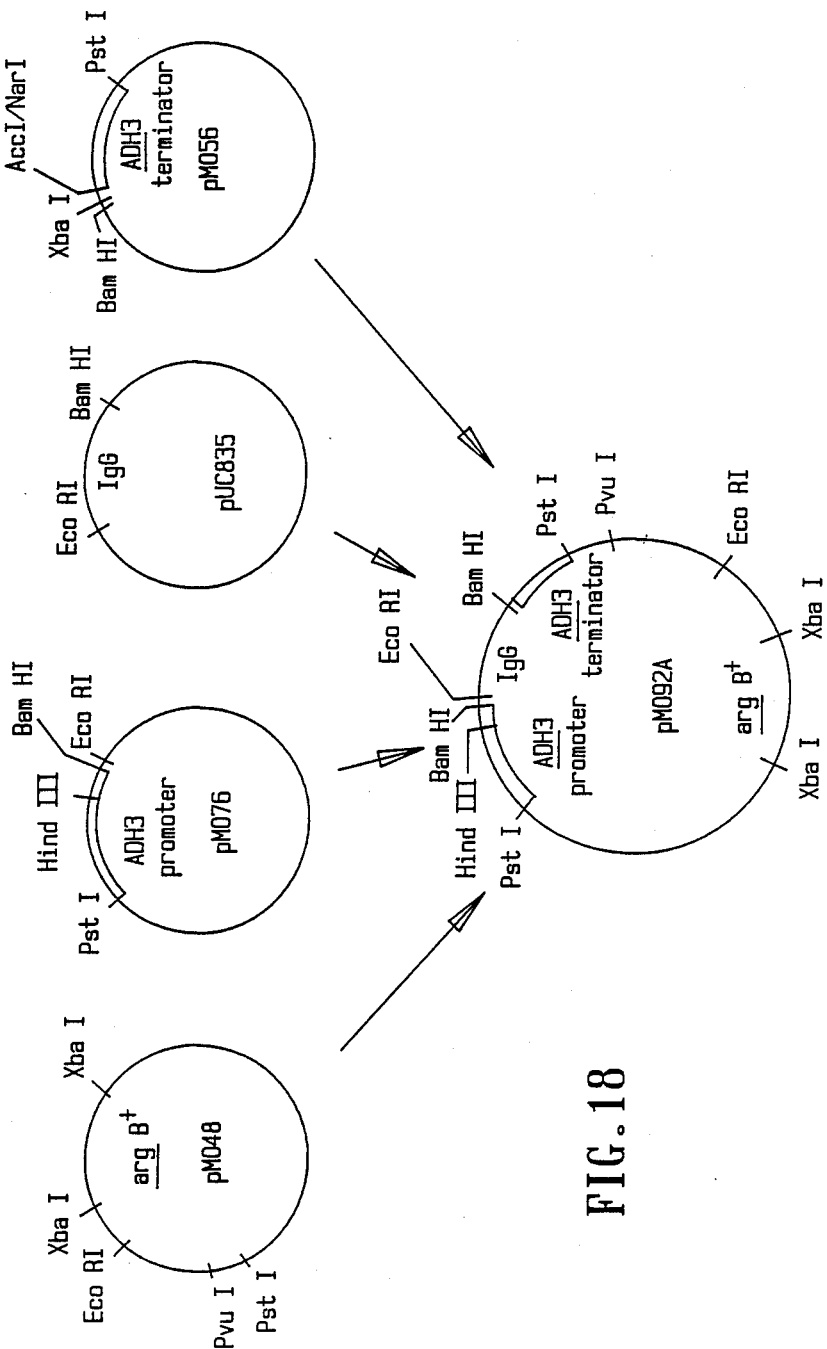
FIG. 18 illustrates the construction of expression vector pM 092A.

Referring to FIG. 18, the 1.1 kb PstI-EcoRI fragment of pM076 was ligated to the EcoRI-BamHI human IgG cDNA from pUC835 and the BamHI-PstI fragment of pM056 in the PstI site of pM048 and designated pM092. *E. coli* cells containing pM092 were selected for resistance to tetracycline and screened for ampicillin sensitivity. The orientation of the Pst I fragment in pM092 was determined and a plasmid designated pM092A was selected for transformation of *A. nidulans*.

EXAMPLE 5

Construction of a GM-CSF Expression Vector for *A. nidulans*

A genomic clone of human GM-CSF was obtained as described by Kaushansky et al. (*Proc. Natl. Acad. Sci. USA* 83: 3101–3105, 1986). Briefly, a once-amplified λ Charon 4A phage library of human genomic DNA was screened using a 70 base oligonucleotide probe derived from the murine and human GM-CSF (hGM-CSF) amino acid sequences. Positive clones were plaque-purified and analyzed by restriction analysis and plaque hybridization. Three clones were found to hybridize to additional probes to the 5' and 3' ends of human GM-CSF cDNA (Wong et al., *Science* 228: 810–815, 1985). These clones were found to be identical and were designated λhGm-CSF.

The GM-CSF genomic clone was then subcloned into the mammalian cell expression vector pD3 and used to transfect cultured COS cells. Messenger RNA was isolated from the transfected cells and used to prepare a cDNA library. pD3 is an SV40 ori-based plasmid vector that permits the expression of exogenous genomic and cDNA fragments under the control of the adenovirus major late promoter. pD3 also comprises an adenovirus tripartite leader sequence, an SV40 enhancer, the polyadenylation signal derived from adenovirus, and a unique BclI cloning site in the vector pML-1 (Lusky and Botchan, *Nature* 293: 79–81, 1981).

To prepare the expression vector, the 2.6 kb BstEII/EcoRI fragment from λhGM-CSF, containing only the region from the TATA box to the polyadenylation signals, was subcloned into the BclI site of pD3 and used to transfect COS cells (Graham and Van der Eb, *Virology* 52: 456, 1973). The three-day COS cell supernatants were assayed for biologically active hGM-CSF by standard human bone marrow culture (Kaushansky et al., ibid). The expression vector, designated pDgGMII (FIG. 19), directed production of $1.9-2.9 \times 10^4$ U/ml hGM-CSF.

Poly A-containing RNA was prepared from transfected COS cell RNA by chromatography over oligo d(T) cellulose. Five ug of poly (A)+RNA (were used to prepare 2.5 ug of first strand cDNA by reverse transcriptase using oligo dT priming. RNAse H and DNA polymerase were used to synthesize second strand cDNA. After blunt-ending the cDNA molecule with T4 DNA polymerase, 2 ug of double-stranded cDNA were ligated to an equal mass of EcoRI linkers. The reactants were digested with EcoRI and the cDNA separated from linker monomers by gel filtration chromatography. 560 ng of cDNA were recovered from the void volume of the column. cDNA was ligated to an equimolar amount of λgtII which had been prepared by digestion with EcoRI and treated with calf alkaline phosphatase. The DNA in the ligation mix was packaged using a λpackaging extract.

Of the $5 \times 10^5$ recombinants prepared from 37 ng of cDNA, $3 \times 10^5$ were screened using a hGM-CSF genomic probe. Overall, 248 plaques hybridized strongly with a nick-translated genomic probe under very stringent wash conditions, suggesting that approximately 0.1% of the clones contained cDNA for hGM-CSF.

Six cDNA clones were plaque-purified and subcloned into pUC13. All of the clones contained a single open reading frame and matched the genomic sequence and previously published cDNA sequence for human GM-CSF. The plasmid was designated pUCcGM. The cDNA clones were also subcloned into M13mp18 and M13mp19 for sequencing.

An Aspergillus expression vector comprising the hGM-CSF cDNA was then constructed. Plasmid pM048 was digested with EcoRI, the cohesive termini were blunt-ended using T4 DNA polymerase, and the plasmid was recircularized and used to transform *E. coli* RR1. Plasmid DNA was isolated from transformants and screened for the absence of the EcoRI site. Plasmids lacking the site were designated pM048-RI. The ADH3 promoter was removed from pM076 as a PstI-EcoRI fragment and the ADH3 terminator was removed from pM056 as an EcoRI-PstI fragment. Plasmid pM048-RI was cut with PstI, joined to the promoter and terminator fragments in a triple ligation, and transformed into *E. coli* RR1. The resultant plasmid was designated pM132.

The GM-CSF cDNA was then inserted into the EcoRI site of pM132. A 548 bp SstI/NcoI cDNA fragment was isolated from pUCcGM. The fragment ends were blunted and EcoRI linkers were added. This fragment was then ligated to EcoRI cut, phosphatased pM132. The ligated DNA was transformed into *E. coli* RR1 and transformants were selected on LB+tetracycline. Mini preps (Birnboim and Doly, *Nuc. Acids Res.* 7: 1513, 1979) of plasmid DNA were digested with EcoRI to verify the presence of the GM-CSF insert and with PstI to determine its orientation. Plasmid pMcGM (FIG. 19) contained the cDNA insert in the correct orientation relative to the promoter and terminator. Plasmid DNA was prepared by CsCl gradient centrifugation for use in transformation of Aspergillus.

EXAMPLE 6

Expression of t-PA, IgG, and GM-CSF in Aspergillus

A. Transformation

*Aspergillus nidulans* was transformed with plasmid DNA by a modification of the procedure of Yelton et al. (*Proc. Natl. Acad. Sci. USA* 81: 1740–1747, 1984). Approximately $10^7$ spores from 5 day old cultures of *Aspergillus nidulans* strain CZ6-1-10 (pabaAl, yA2;

argB; where paba=auxotrophy for p-aminobenzoic acid, y=yellow conidiospore color, arg=auxotrophy for arginine) or strain CZ24-3-25 (pabaAl; argB, areAl; fwAl; where are indicates requirement for ammonium and fw indicates fawn spore color. Ammonium is provided at a final concentration of 5 mM as the tartrate salt.) were innoculated into 400 ml of Aspergillus minimal medium supplemented with 10 mM para-aminobenzoic acid (paba) and 100 mM arginine and were grown at 37° C. in a shaking water bath for 18 hours. The culture was filtered through four layers of sterile cheesecloth, the cells washed with 0.6M MgSO4, and 1 gm of cells was resuspended in 5 ml of osmotic medium (OM) (Yelton et al., ibid) in a 100 ml flask. To the flask were added β-glucuronidase, filter-sterilized Novozyme 234, and BSA, and the suspension incubated at 30° C. with slow shaking. After 90 minutes, the protoplast suspension was transferred to a 30 ml Corex tube. The flask was washed with 5 ml of OM and the wash added to the tube. The mixture in the tube was gently overlayed with 10 ml ST buffer (1.2M sorbitol, 10 mM Tris, pH 7.5) and the tube centrifuged 15 minutes at 7000 rpm in a Sorvall HB4 rotor. The protoplasts were collected from the interface. The ST was removed, the pellet resuspended, and fresh ST overlayed into the tube. The tube was centrifuged and the protoplasts were collected and pooled with those from the first interface. The pooled protoplasts were collected by resuspension in 15 ml of STC buffer (1.2M sorbitol, 10 mM Tris pH 7.5, 10 mM CaCl$_2$), and centrifuged for 15 minutes at 8000 rpm in a Sorvall HB4 rotor. The supernatant was decanted and the protoplasts washed 3 times in 30 ml of STC. The final pellet was suspended in 300 ul of STC.

Plasmid DNA, prepared from *E. coli* transformed with the appropriate expression vector, was extracted twice with phenol, treated with RNaseA, precipitated with ethanol, and resuspended in 25 ul of STC.

Typically, twenty-five ul of plasmid DNA was added to 10$^7$ protoplasts in 100 ul of STC. The solution was gently mixed, and incubated 25 minutes at 37° C. 60% PEG 6000 was then added in sequential aliquots of 0.2 ml, 0.2 ml, and 0.8 ml, with gentle mixing after each addition, and the solution incubated an additional 20 minutes at 37° C. Ten ml of STC were added, the solution gently mixed and centrifuged 15 minutes at 8000 rpm in a HB4 rotor. The pellet was resuspended in 1 ml of complete medium, and the solution incubated at 37° C. on a roller for approximately 2 hours.

One hundred ul aliquots of the protoplast suspension were added to 3.5 ml of 49° C. appropriately supplemented sorbitol agar medium lacking arginine to select for arginine prototrophic colonies. This solution was overlayed onto the same medium and the plates incubated at 37° C. for 3 days.

B. Selection of Transformants and Expression of t-PA

Large, well-sporulating colonies were sampled by removing a small number of spores from a plate using a fine glass needle. The needle was washed in a drop of 0.02% Tween 80 in the center of a minimal+paba agar plate and the suspension spread over the surface of the plate. Plates were incubated 3 days at 37° C. and the purification procedure was repeated.

DNA was then extracted from transformants. Spores of the twice-purified transformants were spread densely over minimal agar containing paba and incubated at 37° C. for 5 days. Spores were harvested by washing the plates with 0.02% Tween 80 (10 ml/per 2 plates). Approximately 2 ml of the spore suspension were added to 40 ml of minimal medium containing paba, and the mixture was incubated 18 hours at 37° C. in a shaking water bath. The mycelium was harvested by filtering the culture through cheesecloth, washed with cold water, frozen in liquid nitrogen, and ground to a fine powder in a pestle and mortar. This was dispersed in 5 ml of extraction buffer (0.2% SDS, 50 mM EDTA, 1 ul/ml diethylpyrocarbonate) and the mixture incubated at 65° C. for 30 minutes. The lysate was centrifuged, 300 ul of 5M KOAc were added to the supernatant, and the mixture was placed on ice for 1 hour. The chilled solution was centrifuged 30 minutes at 23,000 rpm in a Beckman VTi60 rotor and the resulting supernatant was mixed with an equal volume of isopropanol. The solution was centrifuged at 12,000 rpm for 15 minutes in a Sorvall SS34 rotor and the pellet resuspended in 5 ml of TER (10 mM Tris pH 7.6, 1 mM EDTA, 10 ug/ml RNaseA). After extraction with phenol/chloroform/isoamyl alcohol, the DNA was precipitated with isopropanol. The final pellet was resuspended in 30 ul TER.

The genomic DNA from ten independent *A. nidulans* argB+ transformants derived from pMO90B was digested with BamHI and XbaI, Southern blotted and hybridized to the nick-translated BamHI-XbaI tPA cDNA. The positive transformants containing an intact tPA cDNA were designated 90B-2, 90B-5, 90B-6 and 90B-9. The genomic DNA from 90B-2 and 90B-9 were digested with BamHI and PstI, Southern blotted and hybridized to the nick-translated PstI fragment of pMO20.

Fresh spores from 90B-2 and 90B-9 were each harvested in 10 mls of 0.02% Tween 80 from 2 agar plates, each containing minimal-sorbitol medium. The four spore suspensions were each filtered through sterile cheesecloth and 1.7 ml (10$^7$–10$^8$ spores) of each were inoculated into 200 ml of liquid expression medium of the following composition: 1% (v/v) ethanol, 0.1% (w/v) glucose, 100 mM(NH$_4$)$_2$SO$_4$, 50 mM NaPO$_4$ pH 7.0, 11 mM KH$_2$PO$_4$, 7 mM KCl, 2.1 mM MgSO$_4$, 1 mM para-aminobenzoate and various trace elements. The suspensions were grown with shaking (at approximately 400 RPM) at 37° C. for 24 hours. The resulting cultures were then filtered through four layers of sterile cheesecloth and the liquid media were transferred to 250 ml bottles on ice and stored at −80° C. The filtered hyphae were washed with 300 ml of sterile distilled H$_2$O, pressed dry and ground in a mortar and pestle in liquid nitrogen. Approximately half of the powdered frozen hyphae was transferred to a 15 ml Corex tube on dry ice and stored at −80° C.

RNA was extracted from the powdered hyphae as previouly described. The RNA concentrations were determined by spectrophotometry and adjusted by addition of water to give approximately equal RNA concentrations of 7 ug/ul. Twenty micrograms of total RNA each from 90B-2 and 90B-9 were denatured by glyoxal and DMSO, Northern blotted and hybridized to the nick-translated tPA cDNA or the nick-translated ADH3 cDNA. The results indicated that tPA mRNA was present in 90B-2 and 90B-9 at a concentration similar to ADH3 mRNA.

C. Assays for t-PA

The quantitation of plasminogen activator in *A. nidulans* extract, as well as culture filtrate, was carried out using the techniques of enzyme linked immunosorbent assay (ELISA) and fibrin plate assay (Fibrinolysis Assay).

ELISA: For the ELISA, microtiter plate wells were coated with a monoclonal antibody in buffer A (10 ul/well; 6 ug/ml in 0.1M NaHCO$_3$, pH 9.6). The plates were allowed to stand at 37° C. for 1 hour and then were washed three times with buffer B (0.05% Tween 20, 0.05% NaN$_3$, in phosphate-buffered saline). 150 ul of buffer C (0.05% Tween 20, 0.05% NaN$_3$, 1% BSA in phosphate buffered saline) were added to each well and the plates were incubated for two hours at 35° C. to block non-specific binding sites. Plates were then washed three times with buffer B. Test samples were prepared by diluting the material to be tested in buffer C. 100 ul of sample were added per well and the plates were incubated for one hour at 37° C. Wells were aspirated and washed three times with buffer B. 100 ul of a solution of rabbit anti-t-PA antibody (1:1000 dilution) in buffer C were added to each well and the plates were incubated 60 minutes at 37° C. Following three washes with buffer B, 100 ul of goat anti-rabbit IgG coupled to peroxidase (Tago; 1:1000 dilution) in buffer C were added and the plates were incubated at 37° C. for 60 minutes. The plates were washed three times with buffer B and incubated with 100 ul of a solution containing o-phenylenediamine dihydrochloride (0.4 mg/ml) and H$_2$O$_2$ (0.003%) in 0.1M sodium citrate pH 5.0. After five minutes, the reaction was stopped by the addition of 100 ul of 1M H$_2$SO$_4$ to each well and the color development was monitored at 492 nm using an ELISA plate reader. Bowes melanoma cell t-PA was used to develop a standard graph in the range of 0.2-26 ng/ml.

Fibrinolysis Assay: For this assay, the fibrin plates were prepared as described below. 10 ml of a bovine fibrinogen solution (3.0 mg/ml in 0.036M sodium acetate pH 8.4, 0.036M sodium barbital, 0.145M NaCl, $10^{-4}$M CaCl, 0.02% NaN$_3$) were added to 10 ml of a 1.5% solution of low melting temperature agarose in the same buffer at 40° C. To this solution was added 10 ul of bovine thrombin (500 u/ml). The mixture was poured onto a gelbond agarose support sheet (Marine Colloids) and allowed to cool and form a fibrin network in the agarose. Wells were then cut in the agarose. To the wells were added 10 ul of BSA buffer (0.1% bovine serum albumin in phosphate buffered saline) containing either 1 ug, 100 ng, 10 ng, 1 ng, 0 ng of Bowes melanoma t-PA standard, plus 10 ul of BSA buffer, or 10 ul of undiluted or diluted test samples. The plates were incubated at 37° C. for 16 to 18 hours and from the diameter of the clear halo or zone around the well, the amount of biologically active plasminogen activator was estimated.

Plug Assay for Screening Aspergillus Colonies:

Inoculated plates of medium were incubated at 30° C. for 18-20 hours. These plates were overlaid with either nitrocellulose filters (if antibody staining was to be performed) or Whatman filter paper, and incubated at 30° C. for an additional 24 hours. The filters were then removed and from each non-sporulating colony, a plug of constant volume was removed and placed in a well made in a fibrin lysis assay plate. The well was then filled with agarose solution and the plate was incubated at 37° C. Positive colonies were detected by the clearing of the fibrin plate around the plugs.

Colony Blot Immunoassay for t-PA:

Arg+ transformants were picked onto arginine deficient media and grown until small hyphal colonies were present. Nitrocellulose filters were placed on the plates and incubation was continued for another day. The filters were then removed and washed for 30 minutes in 20% methanol, 25 mM Tris pH 8.3, 19 mM glycine, then washed in buffer A (50 mM Tris pH 7.4, 5 mM EDTA, 150 mM NaCl, 5% (w/v) nonfat dry milk). The filters were then incubated in buffer A containing rabbit antiserum against human t-PA for several hours, washed in buffer A and incubated with goat anti-rabbit antibody conjugated to either horseradish peroxidase or biotinylated horseradish peroxidase. For antibodies conjugated to horseradish peroxidase, the filters were washed in buffer B (50 mM Tris pH 7.4, 5 mM EDTA, 0.05% (w/v) NP-40, 1M NaCl, 0.25% (w/v) gelatin, 0.4% (w/v) Sarkosyl), then transferred to horseradish peroxidase developer buffer (17% (v/v) methanol, 43 mM Tris pH 7.4, 120 mM NaCl, 0.05% (w/v) horseradish color reagent, 0.001% (v/v) hydrogen peroxide). For antibodies conjugated to biotinylated horseradish peroxidase, the filters were washed in buffer A, incubated with buffer A containing avidin and biotinylated horseradish peroxidase, washed in buffer B, then placed in horseradish peroxidase developer buffer. Colonies positive for t-PA were identified by the blue staining of the bound horseradish peroxidase.

The *A. nidulans* transformant 90B-9 secreted active tPA into the culture medium at a level of approximately 0.1 mg per liter. The activity of the secreted tPA protein was specifically inhibited by a rabbit polyclonal IgG antibody raised against human tPA.

D. Expression of GM-CSF

The pMcGM plasmid DNA was used to transform *Aspergillus nidulans* strain CZ6-1-10 as described above. DNA was prepared from transformants, digested with EcoRI and PstI, and analyzed by Southern blotting for the presence of the cDNA and intact expression unit.

Total RNA was isolated from five pMcGM transformants and analyzed for the presence of GM-CSF and ADH3 mRNA by Northern blot hybridization (Thomas, *Proc. Natl. Acad. Sci. USA* 77: 5201, 1980). GM-CSF mRNA was relatively abundant in one transformant (designated #10) and detectable at a low level in the other four (#11, #13, #14, #6). Ethanol regulation of GM-CSF and ADH3 mRNA levels was also analyzed by Northern blot hybridization of total RNA samples isolated from cultures grown in the presence of glucose or ethanol. GM-CSF mRNA from transformant #10 was detectable at a low level in glucose and abundant in ethanol, whereas the ADH3 mRNA was not detected in either culture. GM-CSF mRNA from transformant #14 was detectable at a low level in glucose and ethanol, whereas the ADH3 mRNA was detectable in glucose and abundant in ethanol.

To assay for the production of GM-CSF, cultures of Aspergillus transformants (#6, #10, and #14) were grown 8-10 hours in expression medium at 37° C. to allow spores to germinate. Ethanol was added to 1% (v/v) and the cultures were incubated an additional 12-15 hours at 37° C. with shaking. The medium was removed by filtration, placed on ice, then dialyzed with several changes of PBS at 4° C. for two days. Samples of the dialyzed medium were serially diluted in PBS and assayed using freshly extracted bone marrow cells (Kaushansky et al., ibid). All three transformants tested assayed positive at approximately 10 ug GM-CSF per liter of culture medium.

E. Expression of IgG

Similar experiments were performed with pMO92, the plasmid containing the IgG cDNA. The genomic DNA of ten independent *A. nidulans* argB+ transformants derived from pM092A was digested with XbaI, Southern blotted, and hybridized to the nick-translated EcoRI-BamHI IgG cDNA. The four positive transformants were designated 92A-2, 92A-4, 92A-9, and 92A-10. The genomic DNA of 92A-2 and 92A-10 was digested with PstI and EcoRI, Southern blotted and hybridized to the nick-translated PstI fragment of pM020.

Fresh spores from transformants 92A-2 and 92A-10 were harvested as previously described and inoculated into fresh medium. Cultures were grown and harvested and RNA was extracted. Hybridization experiments verified the presence of IgG mRNA in transformant 92A-10.

From the foregoing, it will be appreciated that, although certain embodiments of the invention have been described herein for purposes of illustration, various modifications may be made without deviating from the spirit and scope of the invention. Accordingly, the invention is not to be limited except as by the appended claims.

We claim:

1. A DNA construct capable of directing the expression of higher eucaryotic genes in Aspergillus, said DNA construct containing a transcriptional promoter selected from the group consisting of the *Aspergillus nidulans* ADH3 promoter, the *Aspergillus nidulans* tpiA promoter, the *Aspergillus niger* adhA promoter and the *Aspergillus niger* tpiA promoter operably linked to a higher eucaryotic gene, said gene operably linked to a terminator selected from the group consisting of the *Aspergillus nidulans* ADH3 terminator, the *Aspergillus nidulans* tpiA terminator, the *Aspergillus niger* adhA terminator and the *Aspergillus niger* tpiA terminator.

2. The DNA construct of claim 1 wherein said higher eucaryotic gene is a gene coding for t-PA, IgG, or GM-CSF.

3. A recombinant plasmid capable of integration into the chromosomal DNA of Aspergillus, said plasmid containing a DNA construct capable of directing the expression of higher eucaryotic genes in Aspergillus, said DNA construct containing a transcriptional promoter selected from the group consisting of the *Aspergillus nidulans* ADH3 promoter, the *Aspergillus nidulans* tpiA promoter, the *Aspergillus niger* adhA promoter and the *Aspergillus niger* tpiA promoter operably linked to a higher eucaryotic gene, said gene operably linked to a terminator selected from the group consisting of the *Aspergillus nidulans* ADH3 terminator, the *Aspergillus nidulans* tpiA terminator, the *Aspergillus niger* adhA terminator and the *Aspergillus niger* tpiA terminator.

4. The recombinant plasmid of claim 3 further comprising an Aspergillus chromosomal DNA sequence, wherein said DNA sequence facilitates integration of said plasmid into the chromosomal DNA.

5. The recombinant plasmid of claim 3 wherein said higher eucaryotic gene is a gene coding for t-PA, IgG, or GM-CSF.

6. An Aspergillus culture transformed with a DNA construct capable of directing the expression of higher eucaryotic genes in Aspergillus, said DNA construct containing a transcriptional promoter selected from the group consisting of the *Aspergillus nidulans* ADH3 promoter, the *Aspergillus nidulans* tpiA promoter, the *Aspergillus niger* adhA promoter and the *Aspergillus niger* tpiA promoter operably linked to a higher eucaryotic gene, said gene operably linked to a terminator selected from the group consisting of the *Aspergillus nidulans* ADH3 terminator, the *Aspergillus nidulans* tpiA terminator, the *Aspergillus niger* adhA terminator and the *Aspergillus niger* tpiA terminator, said culture producing the protein product of said higher eucaryotic gene in recoverable amounts.

7. The transformed culture of claim 6 wherein said higher eucaryotic gene is a gene coding for t-PA, IgG, or GM-CSF.

8. A method of producing protein via expression of higher eucaryotic genes in Aspergillus, comprising:
   introducing into an Aspergillus host a recombinant plasmid capable of integration into the chromosomal DNA of Aspergillus, said plasmid containing a DNA construct capable of directing the expression of higher eucaryotic genes in Aspergillus, said DNA construct containing a transcriptional promoter selected from the group consisting of the *Aspergillus nidulans* ADH3 promoter, the *Aspergillus nidulans* tpiA promoter, the *Aspergillus niger* adhA promoter and the *Aspergillus niger* tpiA promoter operably linked to a higher eucaryotic gene, said gene operably linked to a terminator selected from the group consisting of the *Aspergillus nidulans* ADH3 terminator, the *Aspergillus nidulans* tpiA terminator, the *Aspergillus niger* adhA terminator and the *Aspergillus niger* tpiA terminator;
   growing said Aspergillus host in an appropriate medium so that said host produces the protein product of said higher eucaryotic gene in recoverable amounts; and
   isolating the protein product of said higher eucaryotic gene from said Aspergillus host.

9. The method of claim 8 wherein said higher eucaryotic gene is a gene coding for t-PA, IgG, or GM-CSF.

10. A transcriptional promoter capable of directing the expression of a heterologous gene in Aspergillus wherein said promoter is selected from the group consisting of the *Aspergillus nidulans* ADH3 promoter, the *Aspergillus nidulans* tpiA promoter, the *Aspergillus niger* adhA promoter and the *Aspergillus niger* tpiA promoter.

* * * * *